(12) United States Patent
Nadav

(10) Patent No.: US 7,819,661 B2
(45) Date of Patent: Oct. 26, 2010

(54) ORTHODONTIC APPLIANCE AND METHOD

(75) Inventor: Orit Nadav, Jerusalem (IL)

(73) Assignee: DROR Ortho-Design Ltd., Jerusalem (IL)

( * ) Notice: Subject to any disclaimer, the term of this patent is extended or adjusted under 35 U.S.C. 154(b) by 0 days.

(21) Appl. No.: 11/532,319

(22) Filed: Sep. 15, 2006

(65) Prior Publication Data

US 2007/0065768 A1    Mar. 22, 2007

Related U.S. Application Data

(63) Continuation-in-part of application No. PCT/IL2005/000321, filed on Mar. 21, 2005.

(30) Foreign Application Priority Data

Mar. 25, 2004   (IL)   ................................. 161102
Jun. 2, 2004    (IL)   ................................. 162313

(51) Int. Cl.
    *A61C 3/00*    (2006.01)
(52) U.S. Cl. ............................................. 433/18
(58) Field of Classification Search ............ 433/6, 433/7, 18, 21, 24, 215; 128/859, 862
    See application file for complete search history.

(56) References Cited

U.S. PATENT DOCUMENTS

| | | | |
|---|---|---|---|
| 3,827,146 A * | 8/1974 | Wallshein ..................... 433/7 |
| 3,975,825 A | 8/1976 | Smith et al. |
| 4,330,273 A | 5/1982 | Kesling et al. |
| 4,484,895 A | 11/1984 | Smiley et al. |
| 4,793,803 A * | 12/1988 | Martz ............................. 433/6 |
| 4,799,884 A * | 1/1989 | Bergersen ..................... 433/6 |
| 5,055,039 A * | 10/1991 | Abbatte et al. ............... 433/24 |
| 5,975,893 A | 11/1999 | Chishti et al. |
| 6,604,943 B2 * | 8/2003 | White ............................ 433/21 |
| 7,182,596 B2 * | 2/2007 | Paulus .......................... 433/6 |
| 2003/0013062 A1 | 1/2003 | White |
| 2003/0190575 A1 | 10/2003 | Hilliard |
| 2003/0224311 A1 | 12/2003 | Cronauer |
| 2004/0067463 A1 * | 4/2004 | Rosenberg .................... 433/6 |

FOREIGN PATENT DOCUMENTS

DE    28 40 370    3/1980

* cited by examiner

*Primary Examiner*—Cris L Rodriguez
*Assistant Examiner*—Sunil K Singh
(74) *Attorney, Agent, or Firm*—Stein McEwen, LLP

(57) ABSTRACT

An orthodontic appliance for realigning one or more teeth in the intra oral cavity of a subject, includes a base having formed therein one or more guiding cells arranged to fit over a preselected tooth sought to be realigned from an initial position to a final position, each said guiding cell including a guiding structure defining a predetermined trajectory specific to the preselected tooth, along which the tooth is sought to be moved from the initial position thereof to the final position thereof; and apparatus, arranged within each guiding cell, for urging a predetermined tooth along its trajectory.

20 Claims, 15 Drawing Sheets

Section V-V

Section U-U

Section V-V

Section U-U

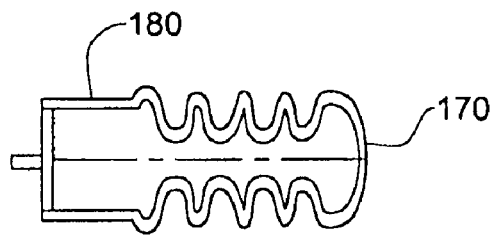
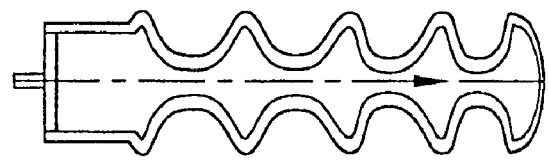
FIG. 9A　　　　　　　　　FIG. 9B
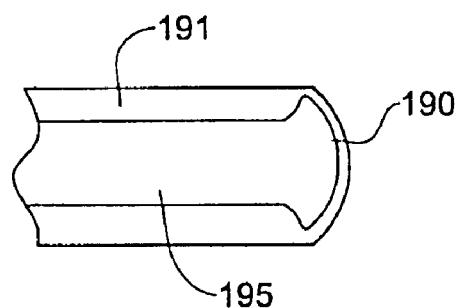
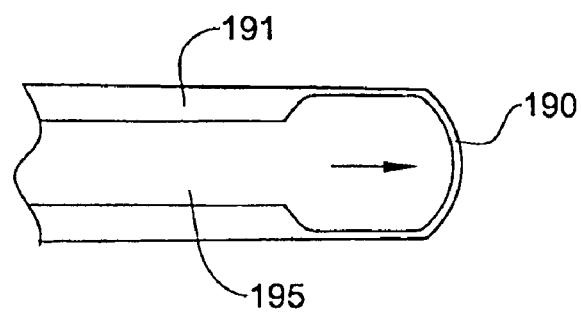
FIG. 10A　　　　　　　　FIG. 10B
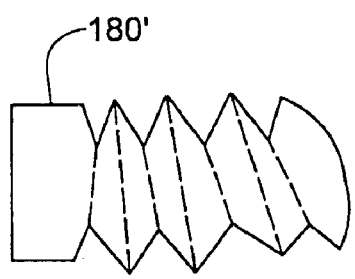
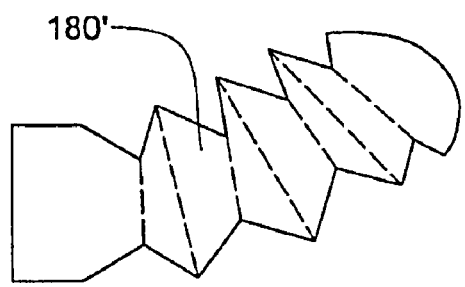
FIG. 11A　　　　　　　　FIG. 11B

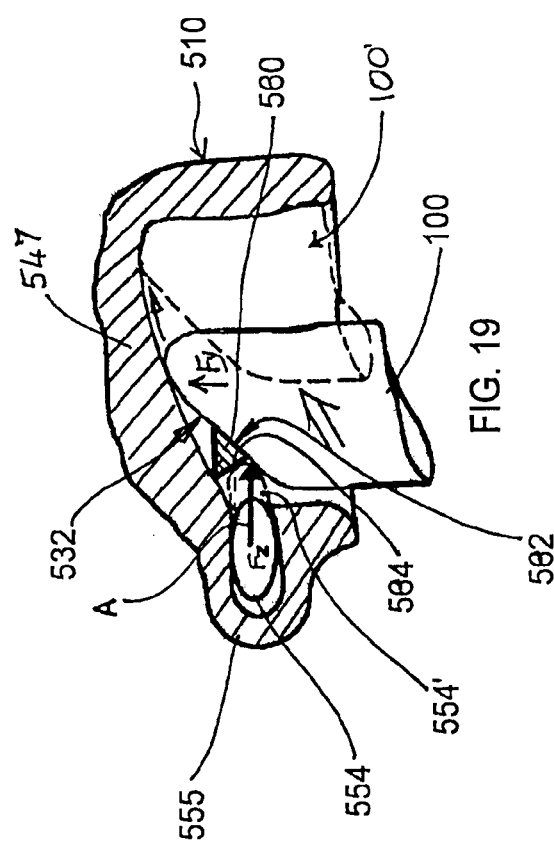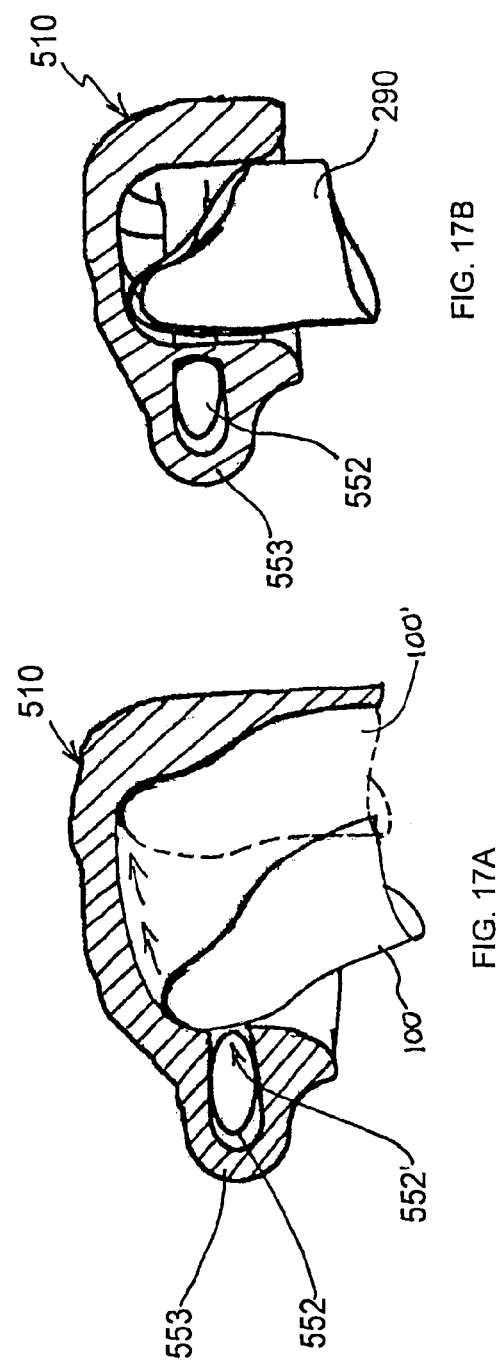

ORTHODONTIC APPLIANCE AND METHOD

RELATED APPLICATION

This application is a continuation-in-part of International Application No. PCT/IL2005/000321 filed Mar. 21, 2005, which is hereby incorporated herein by reference.

FIELD OF THE INVENTION

This invention relates generally to the field of orthodontic appliances. More specifically, the present invention relates to a custom-made removable device for orthodontic treatment in which individual teeth are urged along predetermined paths so as to cause realignment thereof with respect to a desired dentition of a subject.

DEFINITIONS

The term 'dentition,' as employed herein, is used to mean the character of a set of teeth especially with regard to their number, kind, and arrangement.

The term 'desired dentition,' or the like, is used to mean an overall positioning of a set of teeth, deemed to be desirable for a particular subject, by an orthodontist or equivalent professional.

The terms 'lingual-buccal direction' and 'buccal-lingual direction' are used interchangeably, and are used to mean movement of a tooth along a lingual or buccal axis, but are not intended to define the direction of movement therealong, unless specifically stated.

The terms 'initial position' and original position' are used interchangeably to mean the position of a tooth prior to movement into a 'final position.'

The term 'final position' is used to mean a position determined by an orthodontic professional to be the position to which a tooth should be moved.

BACKGROUND OF THE INVENTION

Many devices are known for aligning teeth, and include devices that are permanently fixed with respect to the teeth until treatment is completed, and removable devices that are designed to be worn part time or most of the time, day or night. The former are typically in the form of brackets that are bonded to individual teeth using a suitable adhesive, and a wire urges the teeth towards a final position to effect alignment. The latter are in the form of devices which fit in the intraoral cavity in a manner such as to urge teeth in a desired direction, and which are easily removable and refittable by the patient. The present invention is concerned with such removable devices.

In a first stage for providing such removable devices, a physical plaster model of the patient's dentition is made. The procedure typically requires taking an impression of the teeth to form a negative mold of the teeth, into which a plaster material is poured and set to provide a positive model of the teeth. The positive model is typically dimensionally quite accurate, and faithfully duplicates the anatomy of the patient's intraoral cavity.

Using such a model, which is typically referred to as a study model, the orthodontist is able to study the features of the patient's dentition and to devise a treatment plan to correct any malocclusion or other misalignment. For the purpose of devising such a plan, further models may be produced from the original negative mold, and these models, referred to as working models, may be used for customizing certain orthodontic appliances specifically for the patient. For example, such a working model may be used for bending and positioning wires with respect to teeth, and then for welding the same in place or with respect to a stationary device.

Typically, such appliances comprise an active element that actively generates corrective forces, and a passive element that is designed to remain stationary, serving as an anchor for the active element. Such active elements may comprise, for example, springs that generate orthodontic forces to the teeth or orthopedic forces to the malleable bony structures, and are positioned within a working model during fabrication of the appliance. Ideally, the springs are positioned such that each spring will eventually be in an unstressed state when the tooth it is urging has reached the position desired. This is thus to a great extent dependent upon the skill of the technician that is producing the appliance. When first installed in the intraoral cavity, the springs are each compressed by contact with the corresponding tooth that is intended to be moved by it, by an amount that is a function of the departure of the position of the tooth from the desired position. With the passage of time, each spring deflects its designated tooth, and at the same time releases the stored potential energy of the spring.

In US 2003/0198915, a method is described for fabricating an orthodontic appliance that includes lingual springs. First, a model of the patient's teeth is cast in the conventional manner. One or more ideal grooves are then cut into the lingual surfaces of the model teeth. The location of the floor of the groove reflects the desired position of these teeth after treatment. The orthodontic appliance is cast on the model using the ideal reference grooves on the tooth to position the tooth contacting portion of each lingual spring.

Other methods make use of a digital model of the dentition rather than a physical model. For example, in U.S. Pat. No. 5,975,893, aligner-based therapy philosophies and digital imaging/computer-driven rapid prototyping methods are combined, in which a set comprising a plurality of aligners is formed for a patient. Each upper and lower set of aligners (where required) is worn for a period of time. Each aligner in the set biases a patient's teeth toward an ideal occlusion more aggressively than the previous aligner, and typically between 15 to 25 progressive aligners may be used in one treatment. Over a period of time, the sequential and progressively biased positioners move teeth from their initial maloccluded positions to a near finished and corrected state. Each aligner appliance generally comprises a U-shaped tray or shell having a trough that fits over the teeth. The tray is formed by sucking a thermo-formable sheet material over the reset stone model of the patient's dentition, using heat, pressure and a vacuum force, simultaneously. A first initial data set corresponding to the patient's current dentition is determined using a scanning technique. A final digital model of the dentition in its desired set up after treatment is designed. Intermediate digital models between the initial and final models are then created, and positive tooth models are fabricated from the digital models using rapid prototyping techniques. A conventional pressure or vacuum molding machine is used to produce the appliances from each of the positive tooth models. In US 2002/0042038, a computer implemented system and method implement a dental treatment plan, by specifying tooth movement pattern using a two-dimensional array.

US 2003/0190575 takes a different approach, and employs orthodontic aligner elements that can be secured to openings in a removable aligner appliance to exert the desired forces on selected teeth. This enables aligners to be used in the treatment of some orthodontic cases. In addition, the aligner elements are removable or adjustable, and enables the forces to be maintained, changed, or reactivated over the course of treatment.

SUMMARY OF THE INVENTION

In accordance with the present invention, an appliance and method are provided for moving one or more teeth to a desired set of positions. Each tooth that is to be moved is constrained to move along a predetermined three-dimensional path which extends between an initial position to a final position, while being urged to do so by a suitable force inducing means. The force inducing means provide a motive force for inducing movements which include translations along and rotations about the three orthogonal axes of a Cartesian coordinate system. Of course any other reference coordinate system may be used within the spirit of the invention.

There is thus provided, in accordance with a preferred embodiment of the present invention, an orthodontic appliance for realigning one or more teeth in the intra oral cavity of a subject, which includes:

a base having formed therein at least one guiding cell arranged to fit over a preselected tooth sought to be realigned from an initial position to a final position, each guiding cell including a guiding structure defining a predetermined trajectory specific to the preselected tooth, along which the tooth is sought to be moved from the initial position thereof to the final position thereof, and urging means arranged within each guiding cell for urging a predetermined tooth along the trajectory.

Additionally in accordance with the present invention, the base includes a tray predetermined to fit over a plurality of teeth of a subject, and wherein when mounted onto the teeth of a subject, each guiding cell is seen to have a U-shaped cross-sectional configuration both in a buccal-lingual direction and in a mesiodistal direction.

Further in accordance with the present invention, each guiding cell is operative to engage each tooth sought to be moved from four directions when the tooth is in an initial position, and from five directions when in a final position.

Additionally in accordance with the present invention, each tooth has a buccal surface residing generally in an X-Y plane, a lingual surface residing generally in an X-Y plane, and a cusp formed in a mesiodistal direction and residing in an X-Z plane, and the guiding structure includes:

first and second, mutually opposing inward-facing, upstream and downstream end surfaces, each disposed in a generally X-Y plane; and an alignment portion which includes:

a pair of sidewalls defining third and fourth, mutually opposing inward-facing lateral surfaces, formed integrally with and connecting between the first and second end surfaces, each disposed in a generally Y-Z plane; and a top wall defining a fifth inward-facing surface, formed integrally with and connecting between the first, second, third and fourth surfaces, and disposed in a generally X-Z plane, and wherein, when the guiding cell is positioned over a predetermined tooth sought to be guided from an initial position to a final position, a predetermined one of the first and second end surfaces is operative to contact a predetermined one of the lingual and buccal surfaces of the tooth when the tooth is as at its final position, the other of the first and second end surfaces facing the other of the lingual and buccal surfaces and supporting thereagainst the urging means so as to apply an urging force thereto in a lingual-buccal direction;

the third and fourth inward-facing surfaces are operative to laterally engage at least the cusp of the tooth so as to guide it along its trajectory in the lingual-buccal direction; and the fifth inward-facing surface is operative to abut the top of the cusp of the tooth and to define a surface along which the cusp is permitted to move as the tooth moves from its initial position to its final position.

Further in accordance with the present invention, the urging means is operative to provide a Z force vector along a Z axis, in a generally lingual-buccal direction, and the appliance also includes means mounted onto the tooth surface facing the urging means, for resisting the Z force vector and for converting a portion thereof into a Y force vector, in order to retain the top of the cusp of the tooth in abutting engagement with the fifth inward-facing surface.

Additionally in accordance with the present invention, the means for resisting the Z force vector is a wedge-shaped baffle element affixed to the tooth surface facing the urging means.

Further in accordance with the present invention, the urging means includes:

at least one extendable element joined at one end thereof to the upstream end surface and having a pressure face at a free end thereof for abutting a face of a tooth, the extendable element being extendable from a retracted position to an extended position whereat the free end is at least capable of abutting the face of a tooth; and means for selectably extending the extendable element so as to apply an urging force to the one or more teeth thereby to move each tooth from its initial position to its final position.

Additionally in accordance with the present invention, the extendable element is an inflatable element.

Further in accordance with the present invention, the inflatable element has at least one elongated, balloon-like member adapted for positioning in a mesiodistal direction across one or more teeth sought to be realigned.

Additionally in accordance with the present invention, each balloon-like member is housed in the tray, and includes a discrete inflatable portion for applying an urging force to each of the teeth to be realigned.

Further in accordance with the present invention, each balloon-like member is an inner tube contained within a duct formed integrally with a predetermined sidewall of the tray, and wherein each duct defines at least one inward-facing opening corresponding within each guiding cell, each opening exposing a predetermined portion of the inner tube, thereby to permit inflation of the inner tube through the opening into the guiding cell, so as to apply an urging force to each of the teeth to be realigned.

Additionally in accordance with the present invention, the inflatable element has at least a pair of the elongated, balloon-like members, a first member being a buccal branch of the inflatable element and a second member being a lingual branch of the inflatable element.

Further in accordance with the present invention, the urging means includes at least one spring, cantilevered from the upstream end and having an urging member at a free end thereof for abutting a face of a tooth.

Additionally in accordance with the present invention, the spring is a leaf spring.

Further in accordance with the present invention, there is also provided means for providing a suitable magnetic field within each at least one guiding cell.

Additionally in accordance with the present invention, the urging means is adapted to provide a force at least in the general direction of the trajectory and also towards the top wall.

Further in accordance with the present invention, the force is relatively constant during at least a part of operation of the appliance.

Additionally in accordance with the present invention, the force is provided in a pulsating manner during at least a part of operation of the appliance.

Further in accordance with the present invention, the force is substantially constant at least until the tooth reaches the downstream end.

Additionally in accordance with the present invention, there are also provided static cells adapted for fitting over teeth that are not to be moved and for maintaining such teeth in their initial positions as other teeth are realigned.

BRIEF DESCRIPTION OF THE DRAWINGS

In order to understand the invention and to see how it may be carried out in practice, a preferred embodiment will now be described, by way of non-limiting example only, with reference to the accompanying drawings, in which:

FIGS. 6A, 6B, 6C illustrate in fragmented cross-sectional view the embodiment of FIG. 5A comprising force generating means in the form of a spring, wherein: FIG. 6A—the tooth is absent; FIG. 6B—the tooth is at the original position; FIG. 6C—the tooth is at the final position;

FIGS. 7A, 7B, 7C illustrate in fragmented cross-sectional view the embodiment of FIG. 5A comprising force generating means in the form of an inflatable member, wherein: FIG. 7A—the tooth is absent; FIG. 7B—the tooth is at the original position; FIG. 7C—the tooth is at the final position;

FIGS. 9A, 9B illustrate in transverse cross-sectional view one form of the inflatable means of FIGS. 7A, 7B, respectively;

FIGS. 10A, 10B illustrate in fragmented transverse cross-sectional view another form of the inflatable means of FIGS. 7A, 7B, respectively;

FIGS. 11A, 11B illustrate in transverse side view another form of the inflatable means of FIGS. 7A, 7B, respectively;

FIG. 17A is a cross-sectional view of the appliance and dentition of FIG. 15, taken along the line A-A therein, showing in side profile a single tooth sought to be moved from the illustrated original position to a final position, the tooth engaged by an exposed portion of the inner tube of the buccal branch of the orthodontic force element seen in FIGS. 15-16B;

FIG. 17B is a cross-sectional view of the appliance and dentition of FIG. 15, taken along the line B-B therein, showing in side profile a single, correctly aligned tooth in registration with a non-exposed portion of the inner tube of the buccal branch of the orthodontic force element seen in FIGS. 15-16B.

FIG. 19 is a schematic representation of the lingual branch of the orthodontic force element seen in FIGS. 15-16B, in a position of engagement with the lingual surface of a tooth for buccal realignment.

DETAILED DESCRIPTION OF THE INVENTION

Figure 1:
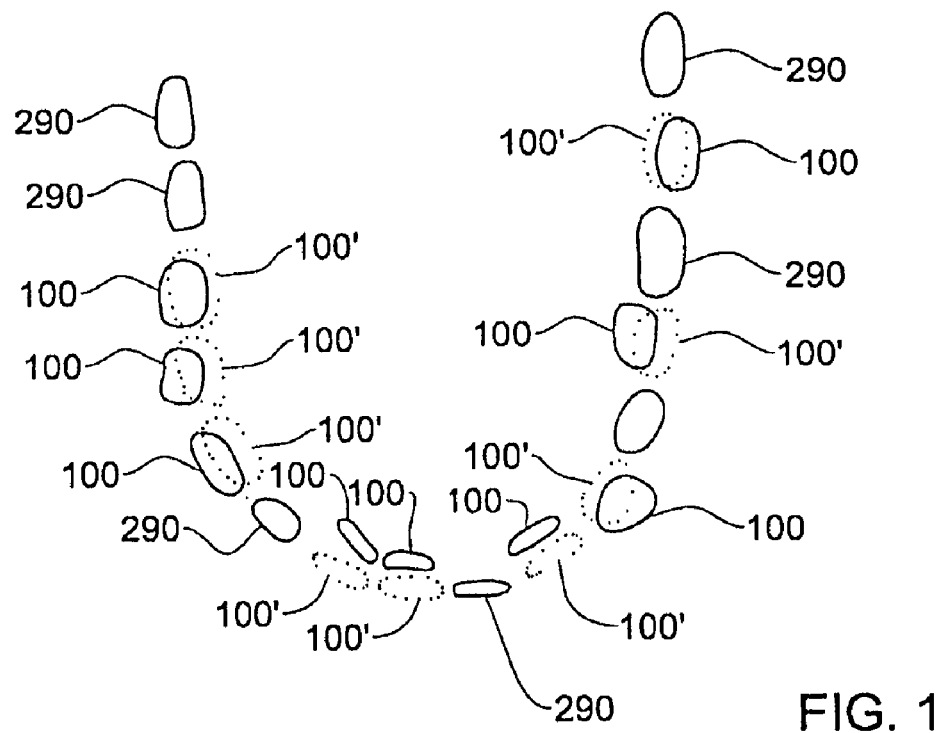
FIG. 1 is a schematic illustration of the original and final positions of a plurality of teeth of a dentition.

Referring initially to FIG. 1, there is illustrated a dentition having a plurality of teeth 100, some of which may need to be moved either lingually or bucally/labially, from an initial or original position shown in full lines, to a final position, shown in broken lines, and indicated by reference numeral 100'.

Figure 2A:
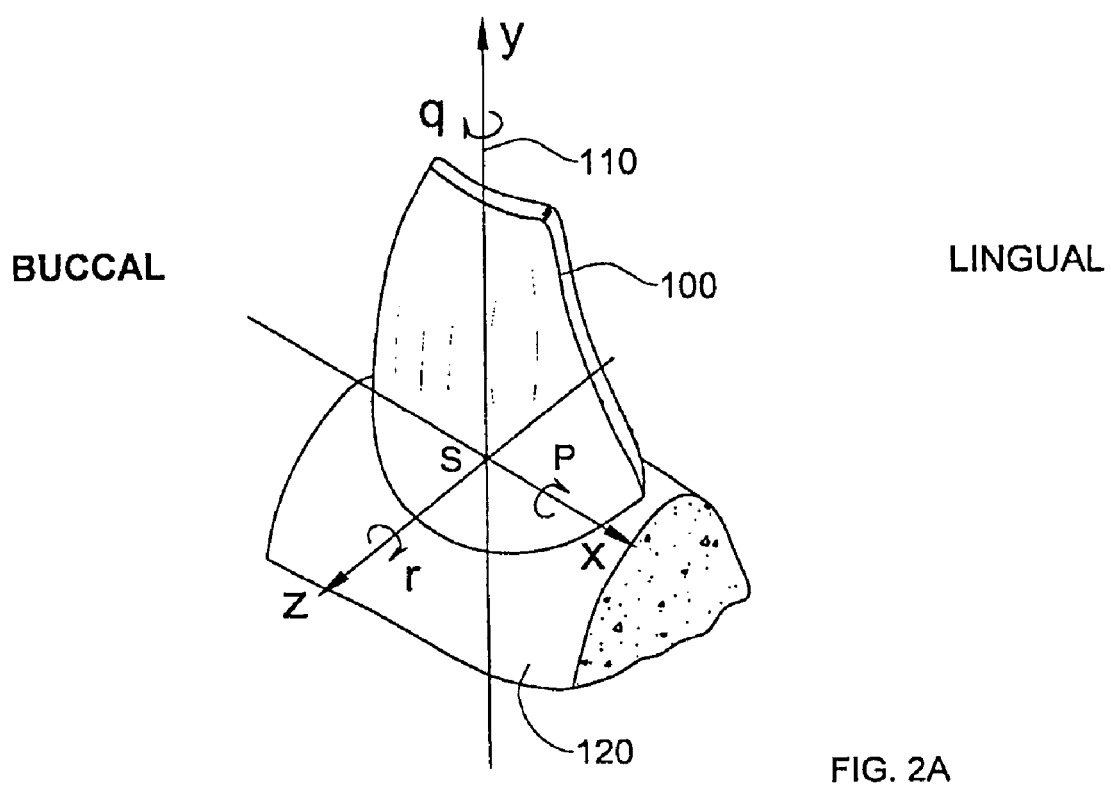
FIG. 2A is an isometric view of a tooth that it is desired to move.

Referring now also to FIG. 2A, an exemplary tooth 100 of the arch of teeth embedded in gum 120 is illustrated as having defined with respect thereto local orthogonal axes x, y and z; the center or origin of the local orthogonal axes is indicated at S. For convenience, for each tooth, the z-axis is aligned in a buccal-lingual direction, the x-axis is aligned approximately along the mesiodistal direction, and the y-axis is mutually orthogonal to the z and x axes.

Figure 2B:
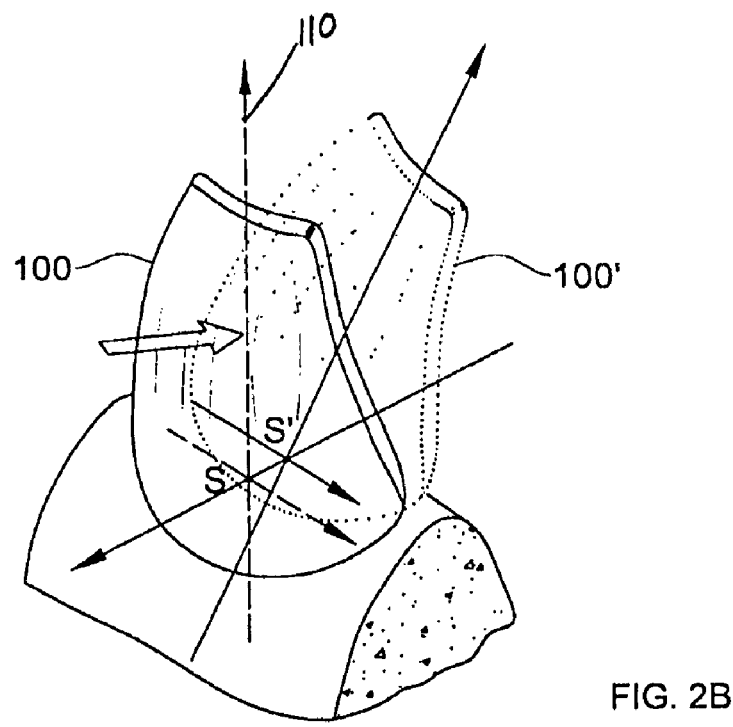
FIG. 2B illustrates the final position of the tooth of FIG. 2A.

Referring now to FIG. 2B, there are shown the original position and final desired position 100' of tooth 100, wherein in order to reach position 100', the tooth 100 must undergo motion composed of the following:

translation of the tooth along one or more of the x, y and z axes;

rotation of the tooth about its center line 110, indicated by the letter q in FIG. 2A; and torque and root angulation, indicated by arrows p, and r, respectively in FIG. 2A.

Clearly, each movement of the tooth 100 may be represented by a combination of translations along the x, y and z-axes and rotations about these axes, and may be idealized in terms of the rotations and translations of point S to reach point S', for example.

Figure 3:
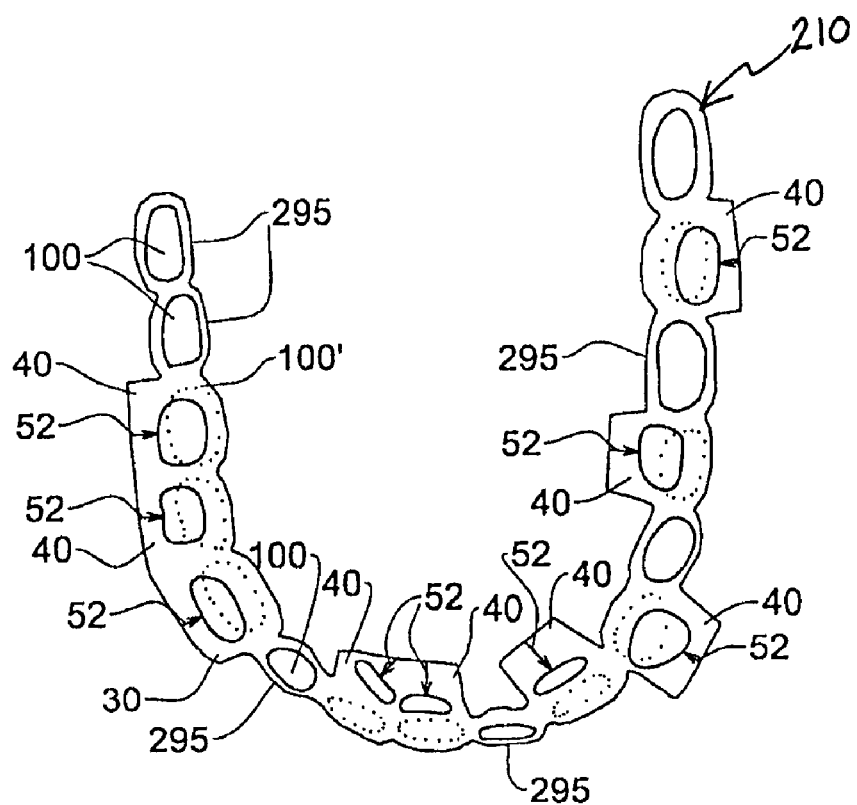
FIG. 3 illustrates schematically an appliance for use with the dentition of FIG. 1, according to a first embodiment of the invention.
Figure 4A:
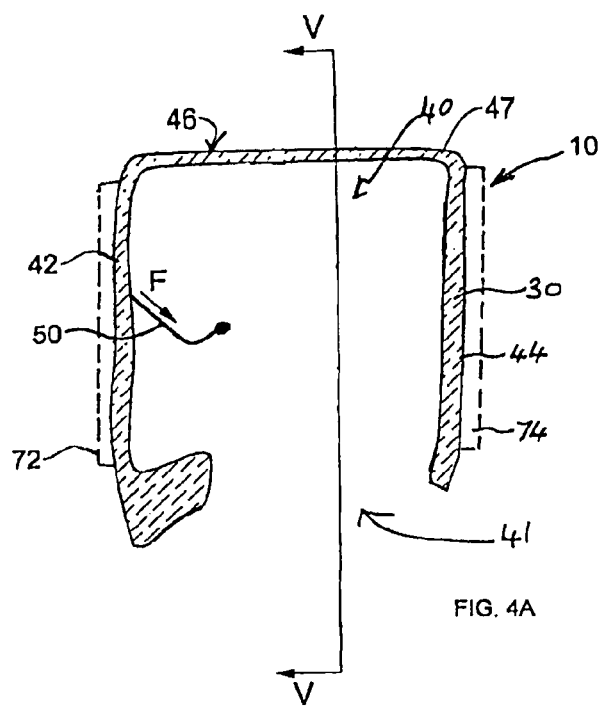
FIG. 4A is a cross-sectional view of a single guiding cell of the dental appliance illustrated in FIG. 3.
Figure 4B:
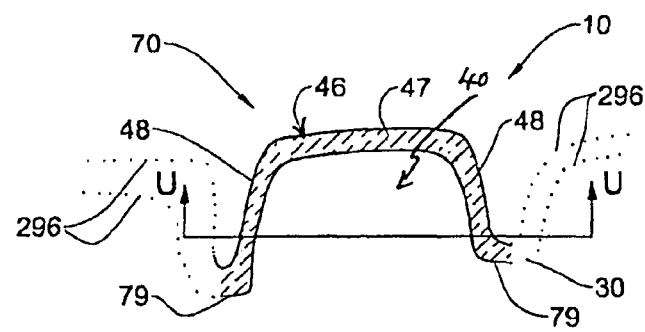
FIG. 4B is a cross-sectional view taken along V-V in FIG. 4A.
Figure 4C:
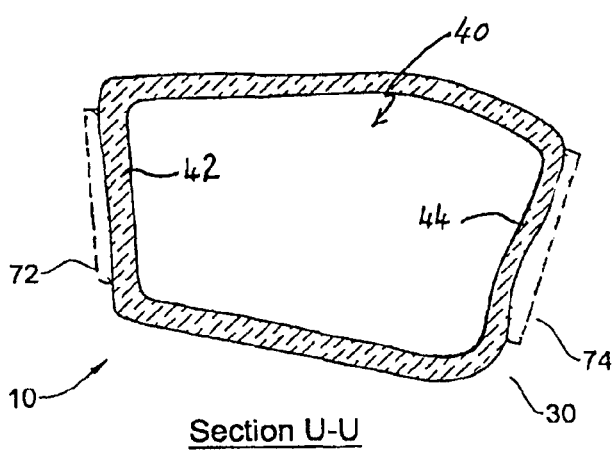
FIG. 4C is a cross-sectional view taken along U-U in FIG. 4B.

Referring now to FIG. 3, there is provided a dental appliance, referenced generally designated 210, which is configured for achieving the simultaneous alignment of each of a plurality of teeth, each along a three-dimensional path, and by use of a single appliance only in which the path of each tooth has been predetermined. A 'plurality of teeth' is at least two teeth, whether adjacent to one another, spaced one from another, arranged in groups, or comprising all the teeth in the same arch of the intra oral cavity, which are acted upon by the appliance to effect alignment. Thus, either all or some of the teeth may be moved by the appliance 210, and some teeth may be moved lingually, while others may be moved in the buccal/labial direction.

The appliance 210 includes a base 30, preferably in the form of a U-shaped tray having formed therein a plurality of guiding cells 40, each of which contains force providing or urging means for moving a tooth over which the cell 40 is positioned, along a three-dimensional path predetermined to be suitable for that particular tooth. Each cell 40 is formed so as to act together with the urging means, so as to define the path along which the tooth is to be moved. The structure of a typical guiding cell 40 and various embodiments thereof, are described in detail hereinbelow.

As seen in FIG. 3, tray 30 may also have formed therein 'static' or non-guiding cells 295 for teeth 290 which are not required to be moved.

Referring now to FIGS. 4A-4C and 5A, 5B and 5C, there is illustrated a single exemplary guiding cell 40 of appliance 10, constructed in accordance with a first embodiment of the invention. It will be appreciated that each cell 40 may be joined laterally to another guiding cell or to a static cell 295, as indicated at broken lines 296 in FIG. 5B, for example.

The guiding cell 40 comprises guiding structure 70 and a force providing element or urging means 50. The guiding cell 40 is adapted to fit over the tooth 100 (FIGS. 5A-5C) that it is desired to move, via an opening 41 (FIG. 4A), and guides the tooth in the desired direction to its final position 100' (FIGS. 5A-5C), as is described in greater detail herein. For the purpose of clarification, the tooth 100 is moved in the direction indicated by arrow A (FIGS. 5A-5C), that is, along a direction approximately from a first face 132 (FIGS. 5A-5C) of the tooth to a second face 134 (FIGS. 5A-5C) of the tooth. The first face 132 may be a lingual surface or a buccal/labial surface of the tooth, and thus the second face 134 may be a buccal/labial surface or a lingual surface, respectively, with respect to the cell 40, depending on whether it is desired to move the tooth generally in the buccal or lingual directions, respectively.

The cell 40 has a first, upstream end surface 42 (FIGS. 4A, 4C, 5A and 5C) substantially opposed to the first face 132 of tooth 100, and that accommodates and aligns the force producing means 50 as required. The cell 40 further comprises a second, downstream end surface 44 (FIGS. 4A, 4C, 5A and 5C) which opposes first end surface 42, and which has a shape complementary to the second face 134 of the tooth 100 that is opposed thereto, and oriented at the desired position corresponding to position 100'. Thus, second face 134 is adapted so as to be in full surface engaging contact with downstream end 44 when tooth 100 is located at its final position 100'. As can be seen also with reference to FIG. 2A, first and second ends surfaces 42 and 44 reside generally in X-Y planes.

The guiding structure 70 has a generally planar alignment element or portion 46 joined at one end thereof to the upstream end 42, and at the other end thereof to the downstream end 44. As best illustrated in FIG. 5B, the alignment portion has a cross-sectional profile which is complementary to the outer profile of the cusp 160 of tooth 100, and is arranged such that the cusp 160 is received within the alignment portion to be in full touching contact therewith. Further, the alignment portion 46 is in a form that is complementary to the locus of the required trajectory of at least the cusp 160, as tooth 100 moves from the original position of the tooth 100 to the final position 100'. This trajectory may require the cusp 160 to translate and rotate by moderate amounts with respect to some or all of the axes, but particularly to translate along the z axis. The trajectory may be determined such as to avoid collision with adjacent teeth, for example, as the tooth moves between the two positions. Thus, side walls 48 of the alignment portion 46 define respective third and fourth mutually opposing inward-facing lateral surfaces each dispose in a Y-Z plane, which are formed integrally with and connect between the first and second surfaces, and act as rails or guides to guide the cusp along the desired trajectory. Finally, it is seen that top wall 47 of the alignment portion defines a fifth inward-facing surface which is formed integrally with and connects between the first, second, third and fourth surfaces so as to be disposed in a generally X-Z plane, and is shaped such as to abut the top of cusp 160.

The ends 79 of the side walls 48 are typically joined in a smooth manner to corresponding ends of the side walls of an adjacent cell.

The cell 40 is preferably made from a dental-compatible material, and one that is rigid or semi-rigid, at least sufficiently rigid to ensure that the cell 40 does not itself deform under the action of force F or the reaction forces thereto with respect to the tooth 100. Suitable materials for cell 40 include, for example, acrylic resin or the like.

Optionally, and as illustrated in FIGS. 4A, 4C, 5A and 5C, each cell 40 may be provided with a magnetic field which potentiate tissue response and improve the biological process that accompanies the movement of tooth 100. Thus, bar or plate magnets 72, 74 may be provided on upstream end 42 and downstream end 44 and properly oriented to provide a suitable magnetic field that penetrates the tooth 100, preferably substantially along direction A. The magnets 72, 74 may be embedded in the walls of the cell 40, or may be attached or bonded thereto. Alternatively, suitable magnetized particles may be comprised in the matrix of material of the cell.

Figure 6A:
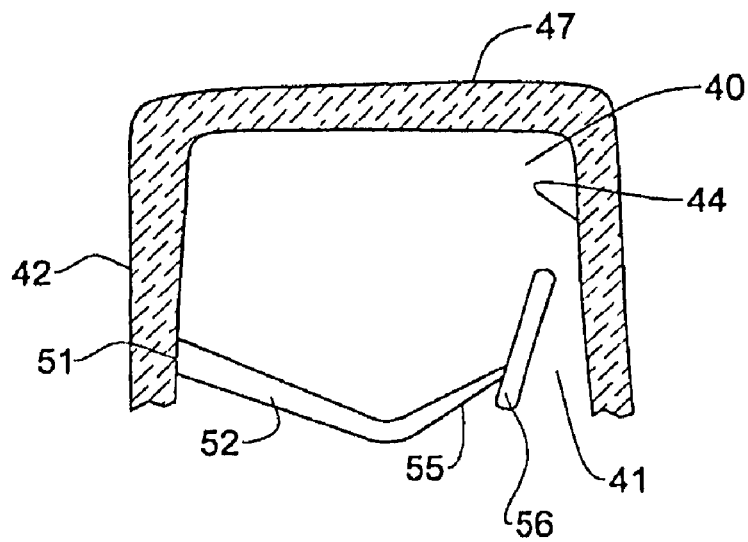
Figure 6B:
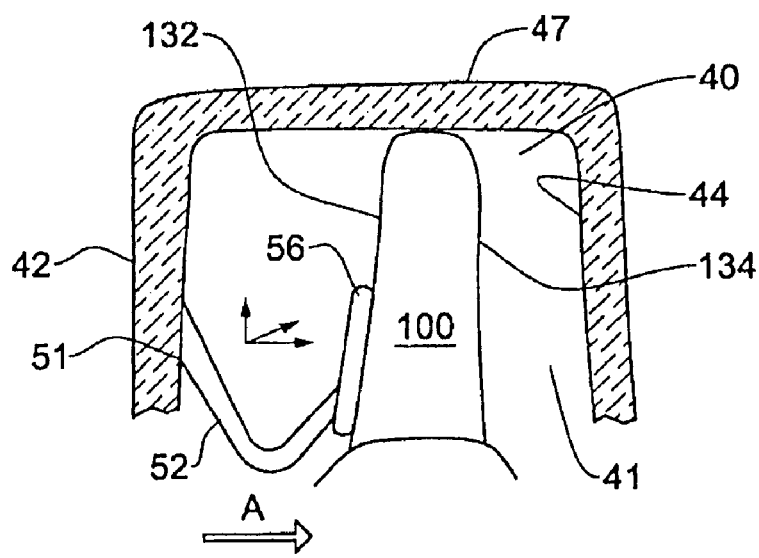
Figure 6C:
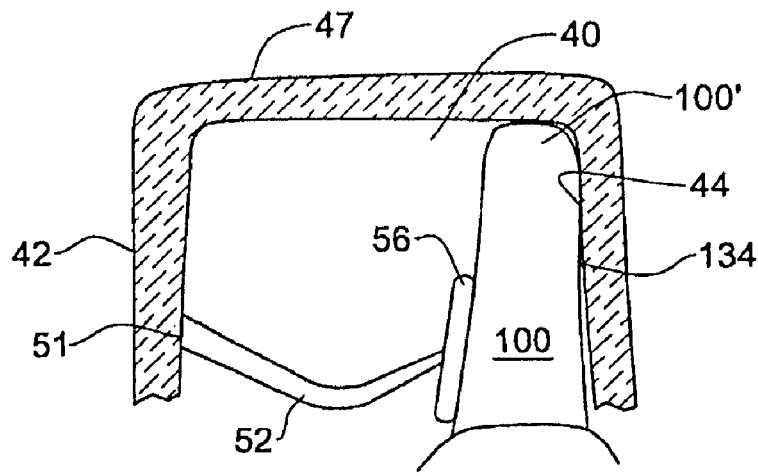

Referring now also to FIGS. 6A-6C, in accordance with one embodiment of the present invention, the force element or urging means 50 is in the form of a mechanical spring 52, such as, for example, a leaf spring, cantilevered at one end thereof from the upstream end 42, and having a free end 55 comprising an urging member 56, as illustrated in FIGS. 6A, 6B and 6C. The urging member 56 may be in the form of a pad or a sphere, or preferably a plate, for example, and the spring 52 is positioned in the cell 40 and shaped such as to urge the first face 132 in the desired direction A such as to reach position 100'. Preferably, the direction A is calculated such that the components of the force F developed by the spring 52 in the x, y and z directions are such as to provide the required translations and rotations with respect to the x, y and z axes. When the final position 100' of the tooth 100 is known, the point of application and relative magnitudes of forces Fx, Fy, Fz required along the x, y and z axes, and their points of application, are determinable.

In practice, it is usually sufficient to provide an approximation of the direction A, so that the force F provided by the spring is in a direction generally correlated with the desired trajectory. Continuous adjustment of the trajectory of the tooth 100 is provided by the alignment portion 46, which is shaped so as to maintain the cusp 160, and therefore the tooth 100, moving along the required direction. Thus, the pushing force F preferably comprises at least one component along the z-axis acting on the tooth 100 near to the gum line, and also component acting along the x-direction and towards the alignment element 46 to maintain the tooth on track along the alignment element 46. In particular, once the tooth has reached position 100', but the orientation of the tooth 100 is not appropriate, continual urging by the spring 52 of the second face 134 against the downstream end 44 eventually seats the second face on the downstream end 44 to fully adopt the position 100', by further rotating the tooth 100 about axis q, for example. Thus, the spring 52 is operative to still provide a pushing force even after the tooth 100 arrives at the required position 100'. Alternatively, the spring 52 may be operative to become substantially unstressed by the time the tooth 100 arrives at the required position 100', and this may be the case when the direction A is fully calculated to achieve this final position.

Optionally, a plurality of springs may be provided within the cell 40.

Preferably, spring 52 is operative to provide a substantially constant force, in terms of magnitude and direction; at least until position 100' is reached by the tooth 100. Accordingly, the spring 52 comprises suitable characteristics such as high springback properties, resistance to permanent deformation, relatively constant force independent of the extension of the spring, and a low modulus of elasticity. The spring 52 may be made from a suitable metal, for example, and may include nickel titanium alloys such as for example Nitinol.

Preferably, the spring 52 is also adapted to permit the appliance 210 to be fitted and removed with respect to tooth 100 numerous times, and is thus ideal for use as a day time, and particularly a night time orthodontic appliance, particularly when the mouth is not being used for eating and drinking, or possibly for talking. Accordingly, the spring 52 may be generally arcuate, as illustrated in FIG. 6A so that when not engaged with a tooth the urging member 56 extends towards the downstream end, and when the tooth is inserted, the spring is compressed to one side such as to provide the required urging force, as described above.

Figure 7A:
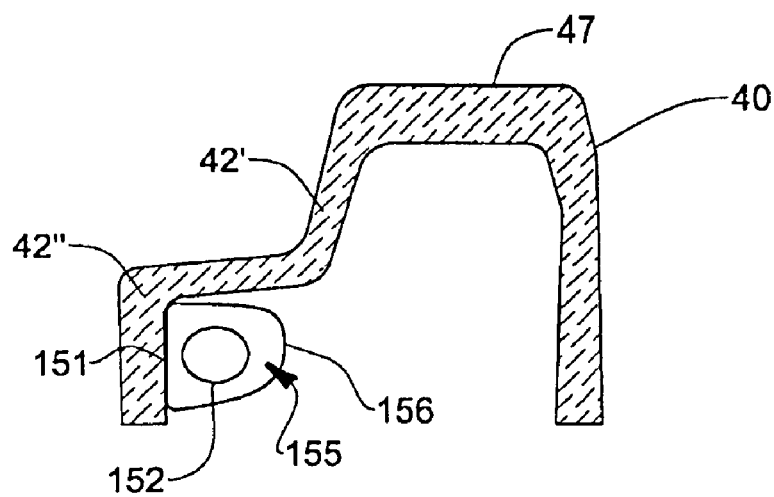
Figure 7B:
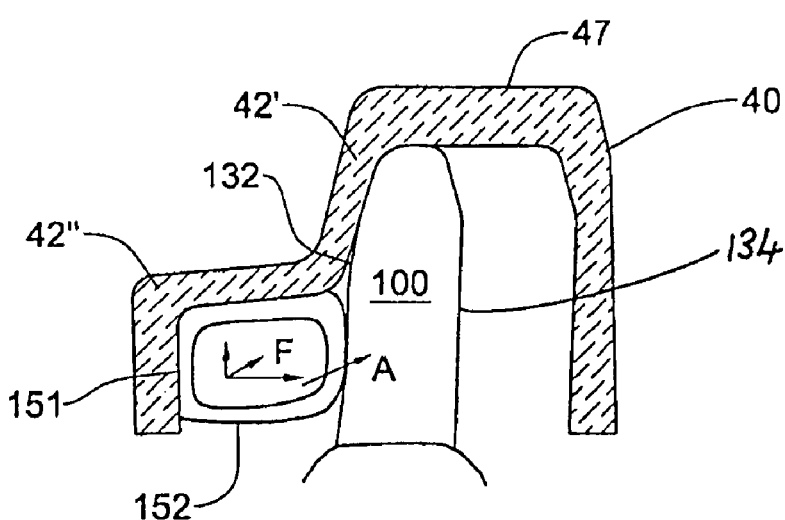
Figure 7C:
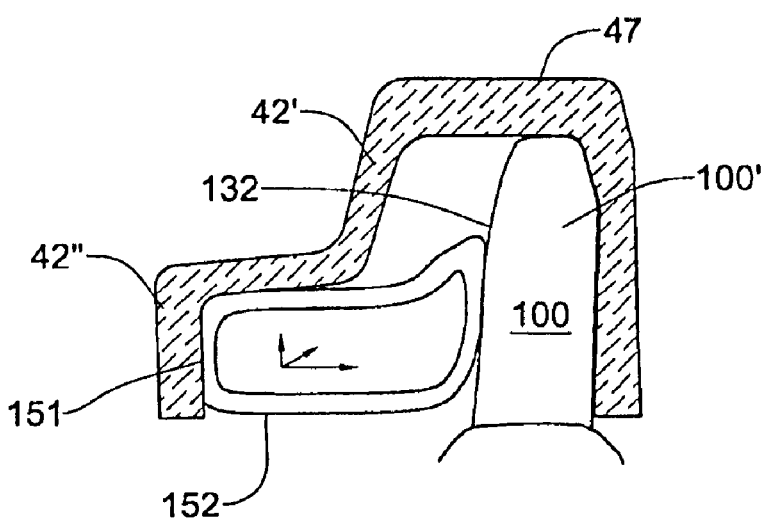

Referring now to FIGS. 7A, 7B and 7C, the force providing means 50 may be in the form of an extendable member, preferably an inflatable member, element or means 152, such as for example a balloon, an inflatable sleeve, or the like, attached at one side 151 thereof to the upstream end 42, and having a free end 155 defining a pressure face 156. The inflatable member 152 is configured to be inflatable from a first, deflated configuration to a second, inflated configuration. In the deflated configuration, the inflatable member 152 does not press against a tooth 100 that is in the cell 40, and may even in fact not be in contact therewith. On the other hand, in the inflated configuration, as seen in FIGS. 7B and 7C, the inflatable member 152 is extended and is in touching contact with first face 132, applying thereto a force such as to urge the tooth 100 in the desired direction A such as to reach position 100'. Preferably, the direction A is calculated such that the components of the force F developed by the inflatable member 152 in the x, y and z directions are such as to provide the required translations and rotations with respect to the x, y and z axes. When the final position 100' of the tooth 100 is known, the point of application and relative magnitudes of forces Fx, Fy, Fz required along the x, y and z axis, and their points of application, are determinable. For this purpose, the inflatable means may be formed such that it will inflate and extend preferentially along a particular predetermined direction, say direction A.

The inflatable means 152 may comprise, for example, a separate balloon or the like for each cell 40, and the balloons of adjacent cells 40 may optionally be interconnected.

Figure 8:
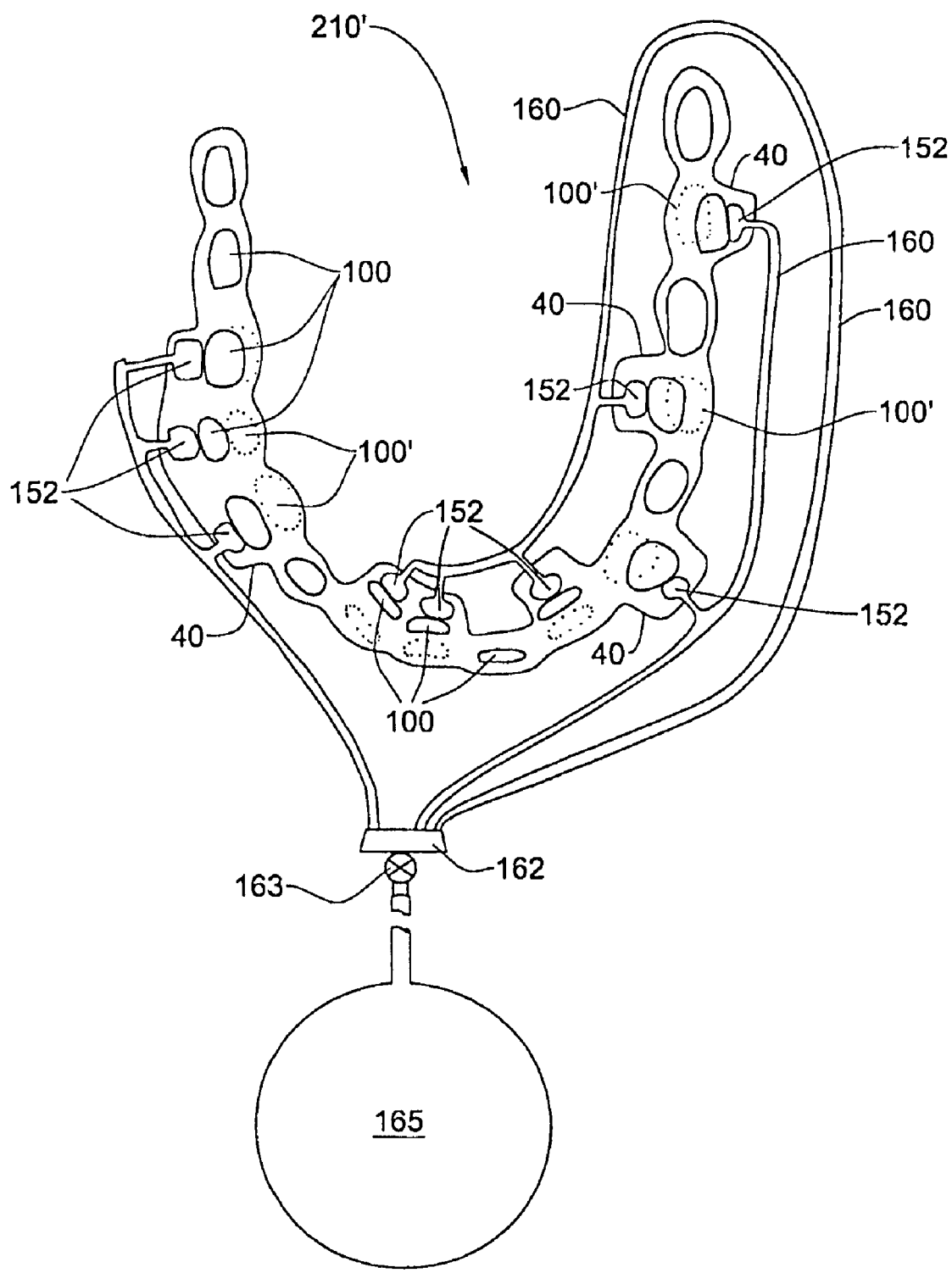
FIG. 8 is a schematic illustration of a manifold-type apparatus incorporating inflatable members as shown in FIGS. 7A-7C, constructed and operative in accordance with an embodiment of the present invention.

Referring now also to FIG. 8, the inflatable means 152 of each cell of each group of adjacent cells in the buccal or lingual sides may be interconnected, for example via fluid pressure lines 160, connected to a suitable fluid supply 165 via a manifold 162. Preferably, the lines 162 are arranged within the appliance 210', and may be formed, for example, as conduits within the walls of the appliance 210'. Alternatively, a single balloon having separate fingers projecting into each of the appropriate cells 40 of a group of such cells on the buccal or lingual sides may be provided for one or more of said groups.

Preferably, the manifold 162 is disconnectable from the fluid supply 165 and includes a suitable valve 163. Thus, when the inflatable means 152 of each cell is appropriately inflated, applying a required force to each tooth 100, the fluid source 165 may be disconnected, which is thus more comfortable for the user, since the lines 160 are preferably mounted or integrally formed with respect to the appliance 210' in an unobtrusive manner. Optionally, when the user desires to remove the appliance 210', the valve 163 is opened, releasing the fluid pressure from the inflatable means, which then deflate accordingly. Alternatively, the appliance 210' may be reconnected to the fluid source 165, and the fluid drained thereinto from the inflatable means 152.

The inflatable means 152 may be pneumatic or hydraulic, and is inflated using any suitable fluid, preferably air or another suitable gas, or a liquid such as, for example, water. The fluid supply 165 may comprise a source of pressurized fluid, and/or a suitable pump for pressurizing fluid in said lines 160. Pressurization and depressurization of the inflatable means 152 may be controlled by a suitable electronic control unit (not shown) operated by the user.

Optionally, the actual pressure provided to the inflatable means 152 may be controlled in any of a number of suitable ways. In one mode of operation, the pressure to the inflatable means is kept constant while the user is wearing the appliance 210'. Thus, as the teeth 100 are moved and the inflatable means expand, the pressure initially would tend to drop, and thus the urging force on the teeth would also drop as well. By maintaining the pressure within the inflatable means constant, however, the force on the teeth 100 is also kept constant.

In another mode of operation, the pressure to the inflatable means is controlled such that the urging force to the teeth is terminated when the teeth arrive at their final positions 100'.

In another mode of operation, the pressure to the inflatable means is varied as desired, for example in the form of periodic pulses, such as to provide a pulsating force to the teeth. The amplitude and frequency of the pulsations may be suitably controlled as desired, preferably by means of a suitable control unit (not shown) operatively connected to a pump (not shown). Such a pulsating force provides benefits to the teeth being treated.

Optionally, it is also possible to provide a measure of the force F exerted on the teeth 100, the force being generally a function of the pressure provided to the inflatable means 152 when the contact area of the pressure face 156 is kept constant. This capability may be used to provide valuable data, which can be collated and used for various applications, including, for example, determining optimal conditions for forces to be applied to teeth.

In practice, and as with the spring 52, it is usually sufficient to provide an approximation of the direction A, so that the force F provided by the inflatable means 152 is applied in a direction generally correlated with the desired trajectory. Continuous adjustment of the trajectory of the tooth 100 is provided by the alignment portion 46 of the cell 40 (FIGS. 4A, 4B, 5A and 5B), which is shaped so as to guide the cusp 160, and therefore the tooth 100, along the required direction. Thus, as seen in FIGS. 5A-5C, the pushing force F preferably comprises at least one component along the z-axis acting on the tooth 100 near to the gum line, and also another component acting along the x-direction and towards the side walls 48 of alignment element 46 (FIGS. 4B and 5B) to maintain the tooth on track along the alignment element 46.

Figure 5A:
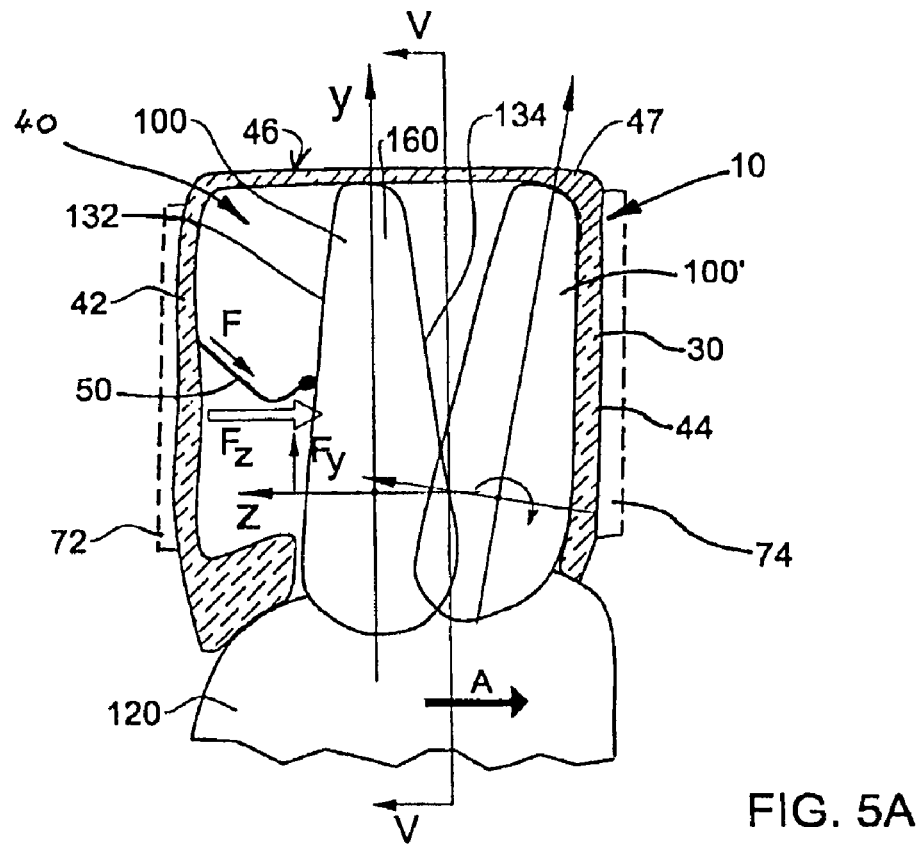
FIGS. 5A-5C are views similar to those of FIGS. 4A-4C respectively, but showing the guiding cell when mounted onto a tooth sought to be moved by the appliance of the present invention.
Figure 5B:
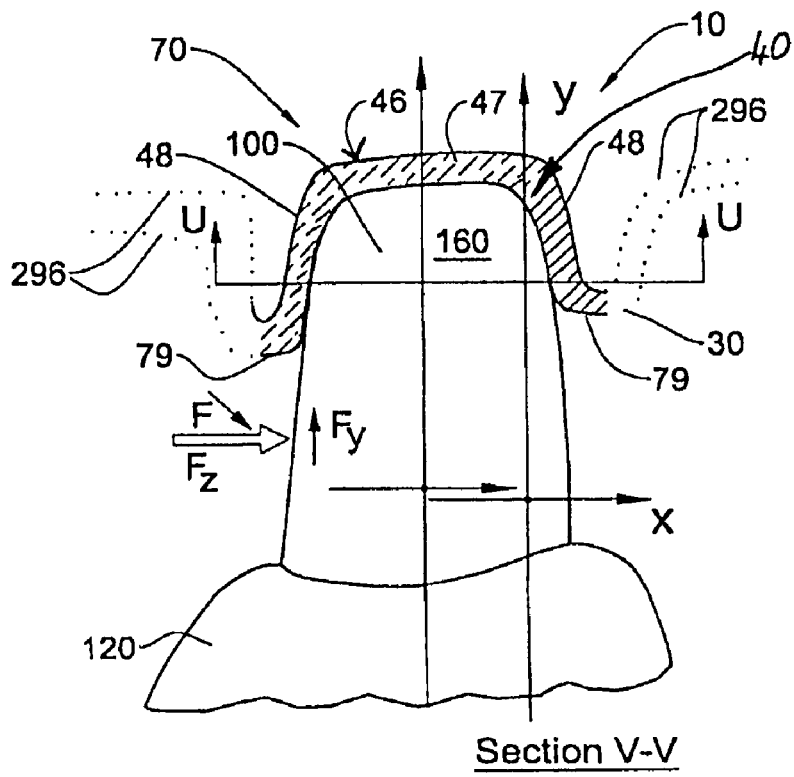
Figure 5C:
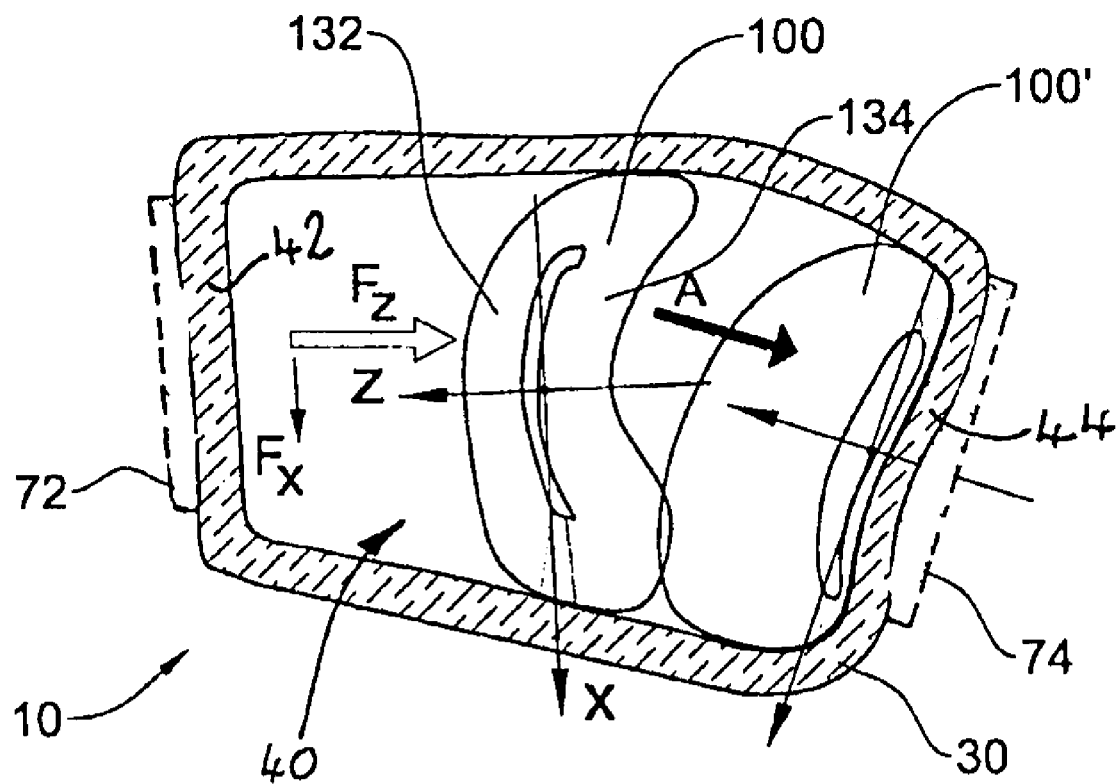

In particular, and referring also to FIGS. 5A-5C, it will be appreciated that once the tooth has generally reached position 100', if the orientation of the tooth 100 is not as required, continual urging by the urging means 50 (FIGS. 4A-5C), exemplified in the present example by inflatable means 152 (FIGS. 7A-8) against first face 132 of tooth 100 causes a corresponding urging of the second face 134 of tooth 100 against the downstream end 44, and eventually seats the second face 134 in fully abutting contact with downstream end 44, such that the tooth is brought into position 100'. It will be appreciated that this may be achieved by further rotation of the tooth 100 about axis q, for example.

Accordingly, the inflatable urging means 152 may be constructed so as to still provide a pushing force even after the tooth 100 arrives generally at the required position 100', by increasing the pressure so as to effect greater expansion of the inflatable means 152. Alternatively, the inflatable means 152 may be constructed to substantially cease urging the tooth 100 by the time the tooth 100 arrives at the required position 100', such as by, for example, limiting the pressure and thus the expansion of the expansion means and this may be the case when the direction A is fully calculated to achieve this final position.

Referring now to FIGS. 9A and 9B, the inflatable member 152 is preferably formed to provide a substantially constant force, in terms of magnitude and direction, at least until position 100' is reached by the tooth 100. Accordingly, and referring to FIGS. 9A and 9B, the inflatable means may be in the form of an accordion-type balloon 180 or the like, configured to expand primarily along a longitudinal axis 170 of the balloon. Optionally, and as illustrated in FIGS. 11A and 11B the balloon 180' may be biased so that when inflated the balloon curves a little in the upwards direction.

Alternatively, and as illustrated in FIGS. 10A and 10B, the leading edge 190 or other parts of the balloon 195 may be formed having a wall thickness of smaller magnitude than that of other parts 191 thereof, such that inflation of the balloon, and thus direction of the force provided by the inflated part of the balloon, may be set.

Furthermore, the upstream end 42 may be constructed so as to constrain the expansion of the inflatable means as much as possible in a desired direction, and thus may comprise the form illustrated in FIGS. 7A to 7C. In other words, part 42' of the upstream end 42 close to the top wall 47 may be considerably closer to the tooth 100, in its initial position, than another part 42" of the upstream end 42 onto which the side 151 of the inflatable means is attached.

When the inflatable means 152 is in the deflated configuration, this permits the appliance 210' to be fitted and removed with respect to tooth 100 as desired, and is thus ideal for use as a day time, and particularly a night time orthodontic appliance, particularly when the mouth is not being used for eating and drinking, or possibly for talking.

Figure 15:
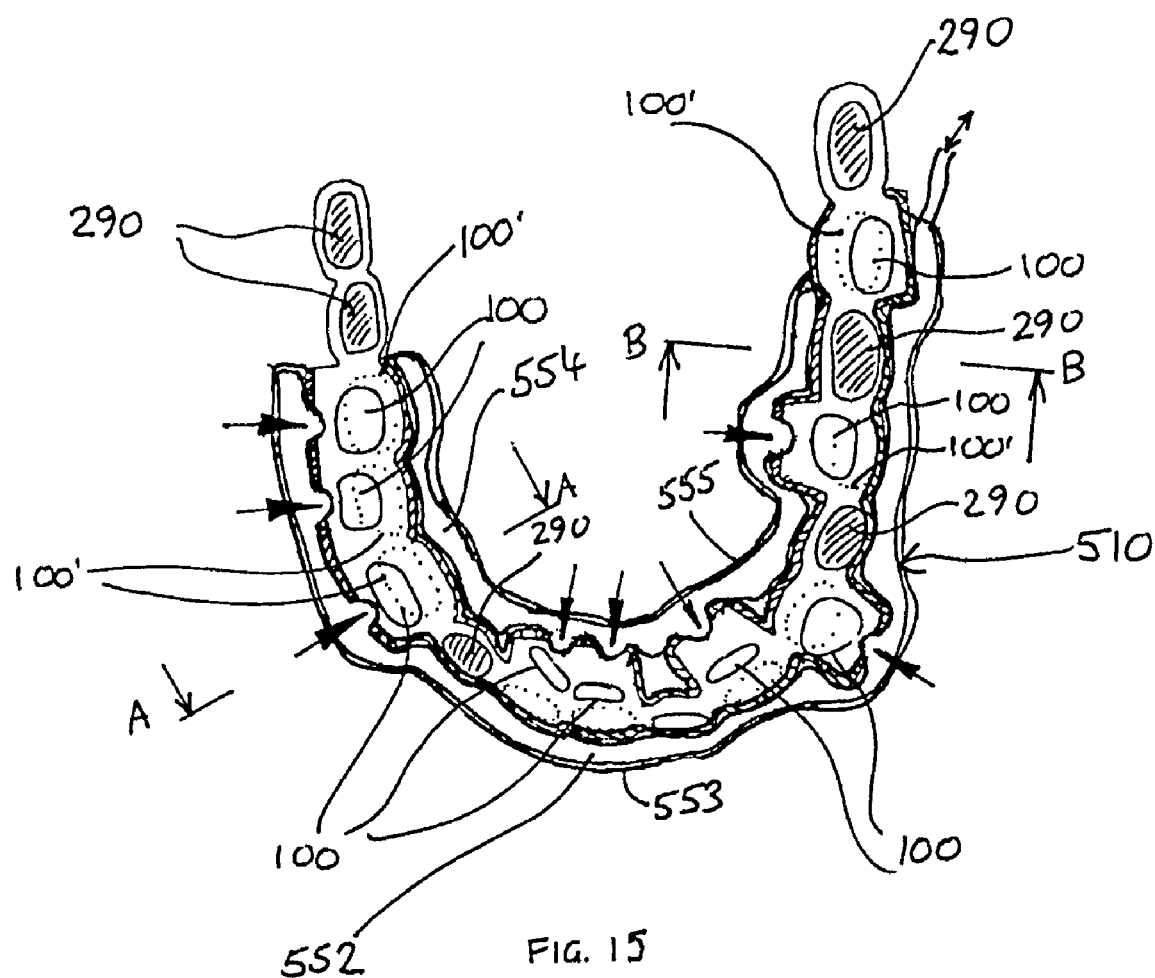
FIG. 15 is a schematic representation of an appliance employing an inflatable force element for use with the dentition of FIG. 1, according to a further embodiment of the invention.

Referring now to FIG. 15, there is illustrated an appliance 510 of the present invention, in which the force providing means thereof is in the form of a pair of preferably interconnected inflatable members, constructed and operative in accordance with an alternative embodiment of the present invention. The present embodiment is generally similar to that shown and described above in conjunction with FIGS. 7A-8, and is only described again herein with respect to features specific to the present embodiment.

Figure 16A:
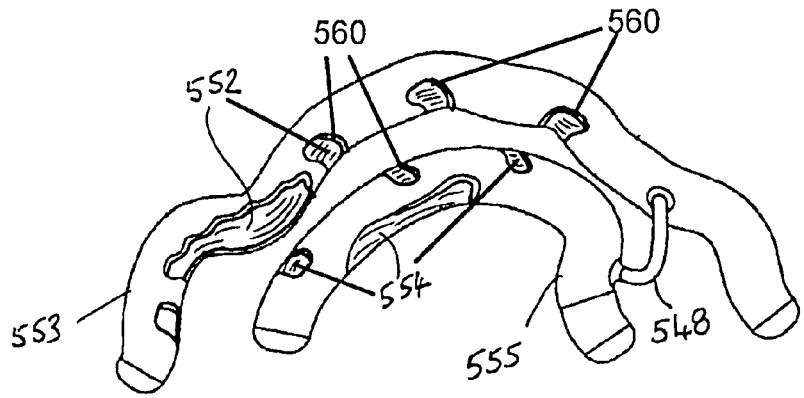
FIGS. 16A and 16B are schematic illustrations of an inflatable orthodontic force element employed in the embodiment of FIG. 15, shown in non-inflated and inflated positions, respectively.
Figure 16B:
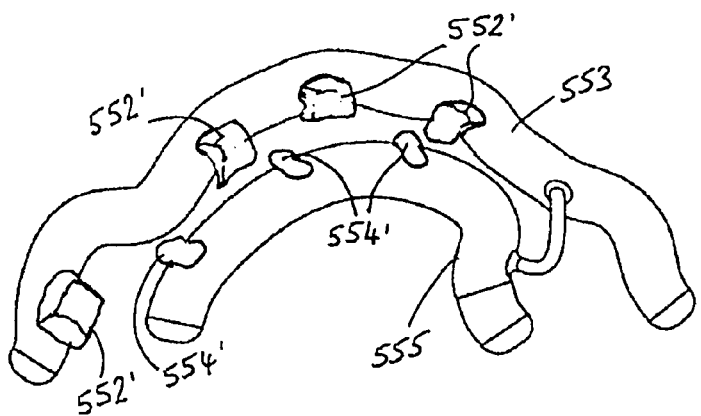

Accordingly, and referring now also to FIGS. 16A and 16B, the inflatable elements, preferably connected by a conduit 548 (best seen in FIG. 16A), are seen to be buccal and lingual branch elements, referenced 552 and 554 respectively, each of which is a selectably inflatable balloon. Buccal element 552 is arranged to lie laterally along teeth 100 so as to selectably apply to predetermined teeth an urging force in a lingual direction; while lingual element 554 is arranged to lie therealong and so as to selectably apply to predetermined teeth an urging force in a buccal direction.

In the present embodiment of the invention, balloon elements 552 and 554 are formed as inner tubes which are contained within ducts 553 and 555 respectively, formed integrally with the sidewalls of tray 30 (FIG. 3). Ducts 553 and 555 are illustrated schematically in FIGS. 16A and 16B, in non-inflated and inflated situations, respectively. Ducts 553 and 555 are formed so as to be closed along most of their length. Openings 560 (FIG. 16A) are formed so as to be in registration with teeth 100 whose position is to be corrected. As seen in FIGS. 15 and 16B, when balloon elements 552 and 554 are pressurized, the only portions thereof that are permitted to inflate are a predetermined plurality of exposed, tooth-urging portions thereof, referenced 552' and 554', respectively, which are permitted to expand through openings 560, as shown schematically in FIG. 16B.

This may also be seen by a comparison of FIGS. 17A and 17B. FIG. 17A illustrates an inflated, tooth-urging portion 552' of buccal balloon element 552, urging tooth 100 in a lingual direction. FIG. 17B, however, is a cross-sectional illustration of appliance 510 at a location whereat no tooth is required to be repositioned. Accordingly, at that location, balloon element 552 is fully enclosed within duct 553, and is thus unable to inflate. Accordingly, at that location, no pressure is applied to tooth 290.

Figure 18A:
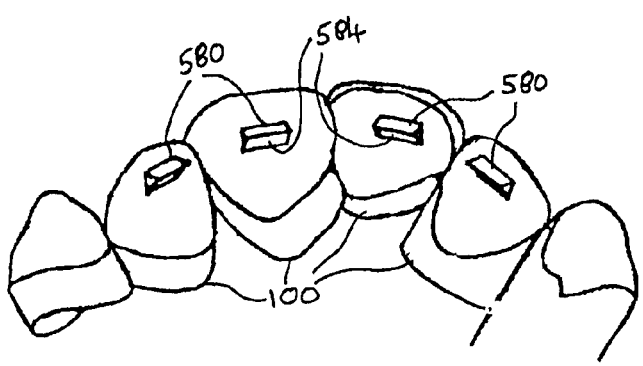
FIG. 18A is a pictorial illustration showing a plurality of teeth for realignment by the lingual branch of the orthodontic force element seen in FIGS. 15-16B, the teeth having baffle members affixed thereto.

Referring now to FIG. 18A, there is seen a plurality of teeth 100 which require repositioning in a buccal direction. Referring also to FIG. 19, the upstream face 532 of the illustrated tooth is sloped and defines an oblique angle with respect to the direction of urging, indicated by the generally lingual-buccal force vector Fz, indicated by arrow A in FIG. 19.

Application of a force vector Fz directly to the illustrated tooth would be liable to cause the tooth to be pushed into the jawbone, thereby causing the top edge of the tooth cusp to separate from the fifth inward-facing surface of top wall 47, rather than to move along it. In order to prevent this, the present invention provides a baffle member 580 which is mounted onto the sloping tooth surface 532 facing the expanded urging portion 554', and is operative to resist the Z force vector Fz, so as to convert a portion thereof into a Y force vector Fy, in order to retain the top of the cusp of the tooth in abutting engagement with the fifth inward-facing surface of top wall 547.

Figure 18B:
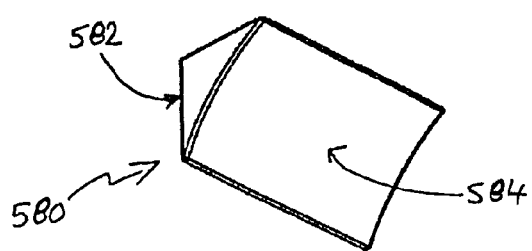
FIG. 18B is a schematic illustration showing, in enlarged detail, a single baffle member shown in FIG. 18A.

Referring now additionally to FIG. 18B, baffle element 580 is preferably a unitary portion of surgical grade rubber or metal, and has a wedge shape defining a first surface 582 for cementing to sloping tooth surface 532, and a second surface 584, typically formed at an acute angle relative to first surface 582, for engaging urging portion 554'. It will be appreciated that baffle element 580 is secured to tooth surface 532 by a suitable adhesive, so as to be substantially immovable relative to the tooth surface.

Alternatively, the inflatable means may be replaced by any other suitable expandable or displaceable means, *mutatis mutandis*, which is displaceable from a first position corresponding to the deflated configuration of the inflatable means 152, to an extended position, corresponding to the inflated configuration of the inflatable means 152. The expandable means may comprise, for example, a piston arrangement capable of being displaced as described, and thus the direction and force of the piston with, respect to the tooth 100 may be controlled. The piston may be driven by means of a fluid such as air or another gas, or water or another liquid, and thus may be hydraulically or pneumatically operated. Alternatively, the piston may be actuated by mechanical means such as my means of a motor and screw jack mechanism, or by electrical means such as a solenoid or the like. Alternatively, the piston may be replaced by any other mechanism or arrangement that provides the required extended and retracted configurations. For example, an expandable means in the form of a displaceable element may comprise a magnetic element attached to the first face 132 of the tooth. A second magnetic element may then be provided in the cell 40, wherein the first and second magnetic elements have like polarities facing each other, providing a repulsive magnetic motive force that urges the tooth along its trajectory. Optionally, the second magnetic element is in the form of an electromagnet, the force and direction of which can be controlled to provide a constant force, a pulsating force, and so on.

The tray 30 can be held in a fixed relationship with the arch or interest in the intraoral cavity by virtue of the forces generated by force providing means of a plurality of cells 40, which act together to hold the tray 30 firmly against the teeth 100. Optionally, the jaw onto which the tray 30 is to be fitted may comprise a number of teeth that do not require to be moved, and thus the tray 30 may comprise a polymeric shell 295, such as shown and described hereinbelow in conjunction with FIG. 12, corresponding to each such tooth, having a cavity that is shaped to receive and resiliently hold the static tooth. The shells 295 thus provide anchor points for the tray 30. Optionally, a base part (not shown) may be provided for holding the tray 30 relative to the intra oral cavity in a fixed relationship. The base part may be adapted to be seated or to fit under the palate or on the floor of the mouth between the base of the tongue and the gingival margin of the gum, depending on whether the appliance 210 is for use with respect to the upper or lower arch, respectively. Such a base part may act as an anchor point and provides a fixed datum, and may be formed as an acrylic mass having an external profile that is complementary to the part of the intraoral cavity in which it is adapted to be fitted during use of the appliance. In the cell 40 illustrated in FIG. 5C, the downstream end 44 may be joined to the base part. In other cells in which the upstream end is on the lingual side, the upstream end may be joined to the base part. Optionally, the tray 30 can be produced integrally with such a base, or these two components may be made separately and bonded or otherwise joined together.

The geometry of the cell 40, and in particular that of the alignment part 46 and the downstream end 44, is determined, and the cell 40 may be manufactured using such a determination, as follows.

Figure 13:
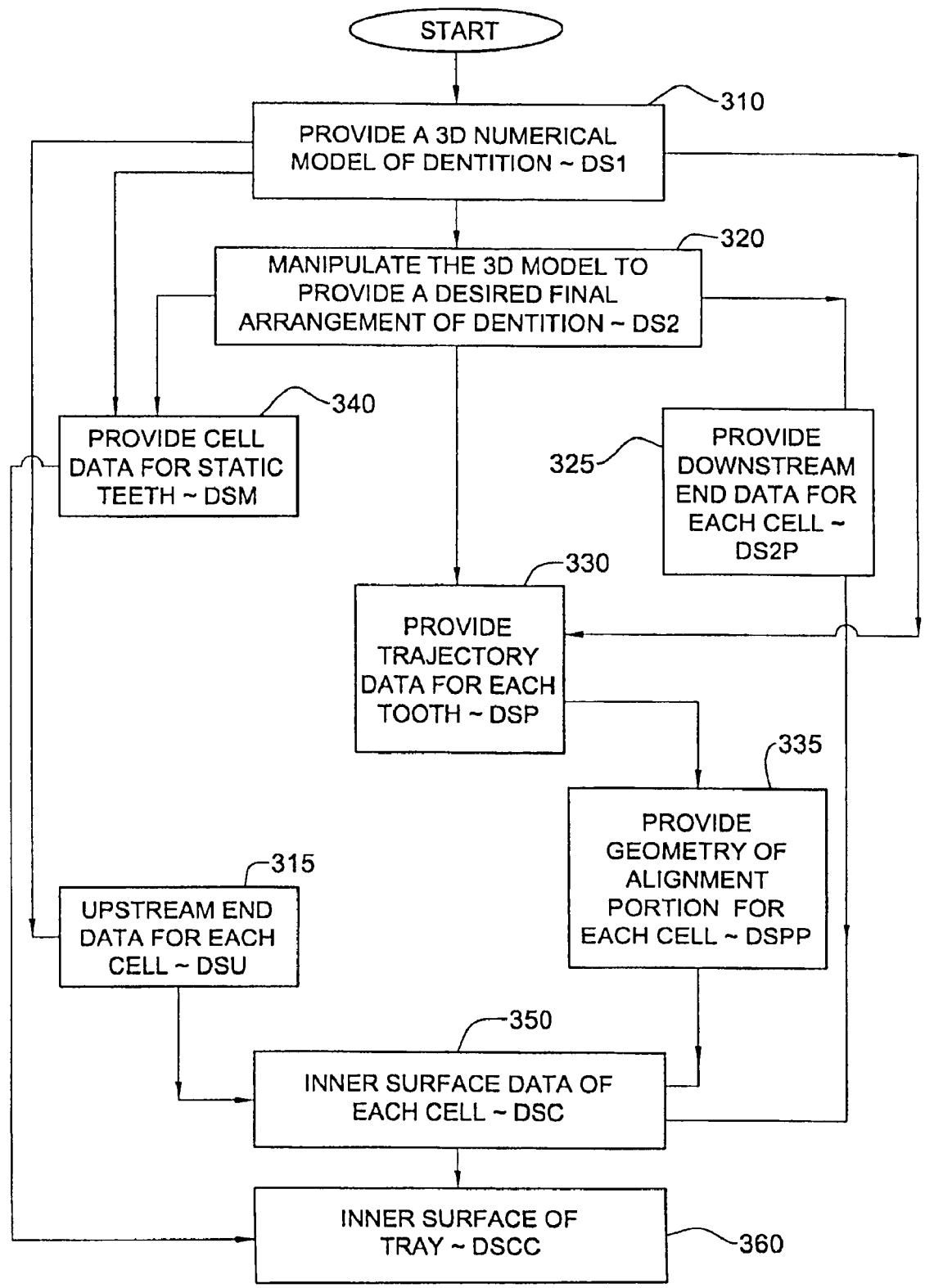
FIG. 13 illustrates a flowchart useful in determining the inner geometry of the cell of the embodiment of FIG. 4.

Referring to FIG. 13, in a first step 310, the three dimensional (3D) structure of the patient's dentition, including tooth 100 and the adjacent teeth, and preferably the full dentition of the jaw on which tooth 100 is located, is determined, and provided in digitized form. This may be accomplished in any number of ways. For example, the intra-oral cavity may be scanned or imaged using technology known in the art, including X-rays, CT, MRI, using direct contact methods, using non-contact methods such as for example those that employ an optical probe. Alternatively, a negative casting of a patient's teeth is obtained in a manner well known in the art, and this is used for preparing a positive cast suitable for scanning or imaging. Alternatively, the negative model itself is scanned or imaged. The dimensional data may be associated with a complete dentition, or of a partial dentition, comprising the tooth 100. Providing a digitized data set DS1 from such scanning or imaging is also known in the art and will not be described further. The digitized data set DS1 is manipulable, and thus allows the next step to be performed using a suitable computer.

In the next step 320, the data set DS1 is manipulated to provide a final tooth arrangement comprising a final digitized data set DS2, in which each tooth 100 is positioned in the desired position 10*f*, for example as described in U.S. Pat. No. 5,975,893, the contents of which are incorporated herein in their entirety. Essentially, the 3D data corresponding to the individual teeth, DST, of the scanned dentition are separated from one another, and the user repositions the DST data for each tooth based on visual appearance, using rules or algorithms, or according to prescriptions provided by the orthodontist.

In the next step 330, and based on the initial data set DS1 and the final data set DS2, the 3D trajectory or path DSP between the initial and final positions of each tooth 100 is mapped and thus determined. The 3D path DSP may take the form of a surface enveloping the locus of positions of the 3D representation of each tooth 100 as it moves from the original position to the position 100'. This path can also be visualized as the path "tunneled" in 3D space by each tooth 100 separately as it moves to position 100'. Such a determination includes ensuring that this path will not adversely affect the disposition of the other teeth in the dentition. The final position 100' for each tooth is typically arrived at by the shortest path possible, consistent in also allowing the other teeth in the arch to move in an optimal manner.

In step 325, a part of DS2, corresponding to the second face 134 and herein referred to as DS2P, provides the 3D data and thus the geometry for the downstream end 44 for each cell 40. In step 335 a part of the DSP data will correspond to the inner geometry of the alignment portion 46. The geometry of upstream end 42 may be constructed according to where the force providing means, such as spring 52 or the inflatable means 152, for example, is to be positioned, what type of spring or balloon is needed, and other factors and considerations may be taken into account, for each cell 40. A digitized representation DSU of the upstream end 42 may thus be created for each cell 40, step 315.

The data sets DS2P, DSPP, DSU for each individual cell are then integrated to provide a dataset DSC representative of the internal surface of each cell 40. For teeth that do not require to be moved, the digital data corresponding thereto DSM in the original dataset DS1 will be substantially identical to that in the final digital dataset DS2, and data set DSM is obtained in step 340.

In step 350, the datasets DSC for each cell 40 and the data sets DSM for the teeth that do not require to be moved (when such teeth are comprised in the arch) are combined to provide a data set DSCC that covers the internal geometry of the tray 30, step 360.

The geometry of the external surface of each cell 40 is generally not of particular importance, other than it should be smooth and minimally interfere with the oral cavity. Typically, the cell 40 is of approximately uniform thickness. Thus, the outer shape of the tray 30 may be calculated by outwardly displacing the surface defined by DSCC by a desired thickness, for example.

It is also possible to provide the location of the force providing means, such as spring 52 or inflatable means 152, for example, within each, cell 40 using the datasets created up to this point. For this purpose, a suitable program can be created that determines the direction and point of application of a force with respect to the tooth 100 such that will provide the required displacement to position 100'. It may be assumed that the direction of the force, as provided by force providing means, will be constant. Alternatively, the direction of this force may move as the force providing means such as a spring is extended or the inflatable means is inflated within the cell 40, and this may be compensated for using appropriate mathematical or numerical tools. According to the type of spring or inflatable means used, the program can then determine the anchoring point 51 of the spring within the cell 40.

Thus, referring to FIG. 1, the current position of the teeth 100 is first measured, and the desired position 100' for each tooth is determined, Referring to FIG. 3, for each tooth 100 that needs to be moved, the precise internal configuration of an individual cell 40 is determined. For teeth 290 which do not require to be moved, a cell 295 can be formed that has an upstream end and a downstream end that correspond to the buccal/labial and lingual faces of the tooth, and thus without an alignment part.

The appliance 210 may then be manufactured using CISTC machining methods, for example, in which the tray 30 may be produced either indirectly (e.g., by manufacturing the molds using CNC techniques) or directly by any suitable material removal operation applied to a suitable material.

Alternatively, the tray 30 is fabricated using other methods. For example, the tray 30 may be fabricated using rapid prototyping techniques, for example based on a stereolithography machine, such as for example Model SLA-250/50 available from 3D System, Valencia, Calif. A liquid or non-hardened resin is hardened into a 3D form that can be separated from the non-hardened liquid or resin to form a positive model of the inner surface of each cell 40 and where appropriate also of shell 295, having received the 3D data set DSCC. A mold for the external surface of the tray 30 is produced in a similar manner to that described for the inner surface, *mutatis mutandis*, and injection techniques are used to provide the tray 30 from the inner and outer models thereof.

Once the tray 30 is completed, the springs 52 can be mounted in each cell 40 using any suitable technique. Alternatively, the cells 40 may be formed integrally with force providing means, such as an integral spring 52 or an integral balloon or the like, when appropriate. Alternatively, the force providing means may be held temporarily in the positive model from which the tray 30 is fabricated, and the springs or inflatable means, or other expandable means, are anchored in the corresponding cells 40 as this is cast or formed with respect to the positive models.

It should be noted that while the geometry of the downstream end 44 and the alignment portion 46, and of the entire inner surface of each cell 40, are advantageously determined using numerical/computer modeling methods and techniques as described, it is also possible to provide the required three dimensional geometries by techniques that are not computer based, for example including manual methods. While the creation of the appliance of the invention starting with the geometric determination thereof using numerical/computer methods is preferred over such manual methods, both methods are within the scope of the invention.

Figure 12:
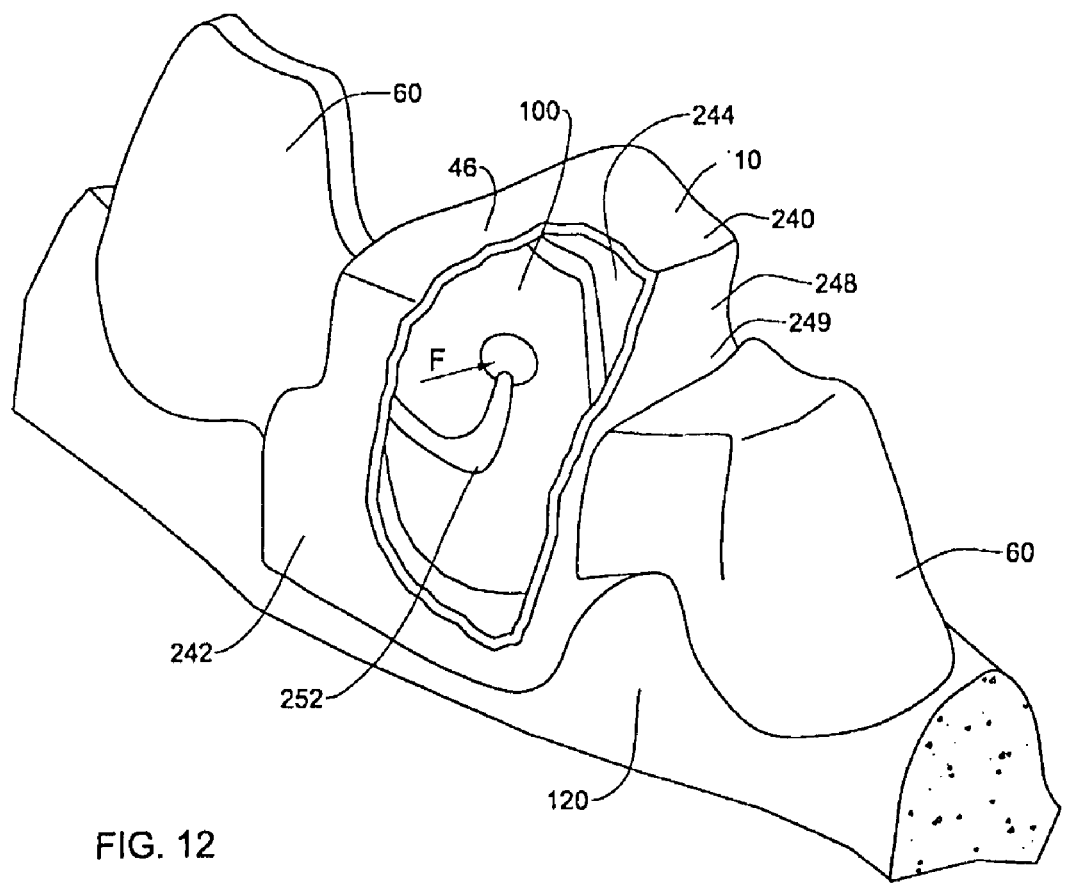
FIG. 12 illustrates in isometric partial sectioned view a second embodiment of the present invention.

Referring now to FIG. 12, a further embodiment of the invention, includes all the elements and features of the first embodiment as described herein, with the following differences, *mutatis mutandis*. In the present, second embodiment, the appliance, designated 10, is adapted for acting on a single tooth The position of the tooth 100 is first measured, and the desired position 100' for the tooth is determined, in a similar manner to that described for an individual tooth 100 in the first embodiment, *mutatis mutandis*. The shape of an individual cell 240 is determined in a similar manner to that described for cell 40, including a spring, *mutatis mutandis*. Preferably, such a cell 240 comprises skirts 249 that project from each of the side walls 248 towards the gums, and which are joined to the upstream end 242 and the downstream end 244, to fully enclose the exposed part of the tooth 100, and prevent foreign matter from entering the same and interfering with the movement of the tooth.

Preferably, and as illustrated in FIG. 12, the appliance 10 may comprise a base part in the form of a pair of polymeric shells 60, each having a cavity that is shaped to receive and resiliency hold the teeth that are adjacent to tooth 100. The shells 60 are bonded to or integrally made with the cell 240 such as to align the downstream end 244 vis-à-vis the desired position 100'.

Figure 14:
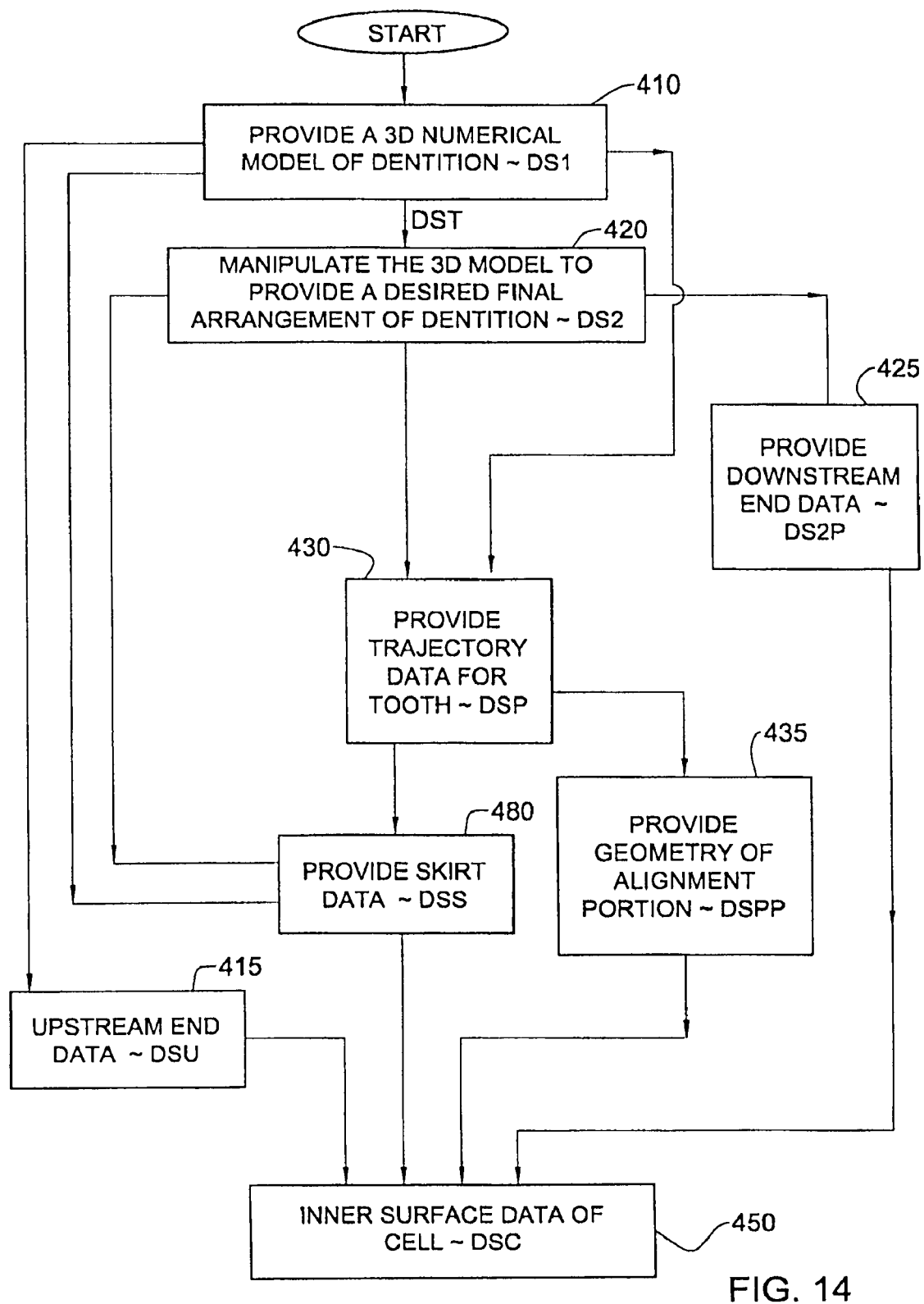
FIG. 14 illustrates a flowchart useful in determining the inner geometry of the cell of the embodiment of FIGS. 7A-7C.

As illustrated in the flowchart of FIG. 14, the internal geometry of the cell 240 may be obtained in a similar manner to that described for the first embodiment, *mutatis mutandis*, with the difference that in FIG. 14 the shape of a single cell 240 is being determined, while in FIG. 13 one of a plurality of cells 40 is being determined. In FIG. 14, like steps to those shown in FIG. 13 are given reference numerals shifted by 100, (for example, step 410 is functionally similar to step 310). Further, and in step 480, the geometry of the skirts 249 may be determined from DS1, DS2 and DSP, such that will not interfere with the movement of the tooth 100, or with adjacent teeth, and a digitized representation DSS of the same is created and incorporated in the data set DSC.

In the claims that follow, the word "comprising" as used throughout the appended claims is to be interpreted to mean "including but not limited to".

While there have been shown and disclosed exemplary embodiments in accordance with the invention, it will be appreciated that many changes may be made therein without departing from the spirit of the invention.

The invention claimed is:

1. An orthodontic appliance for realigning one or more teeth in an intra oral cavity of a subject, comprising:
    a base having formed therein at least one guiding cell arranged to fit over a preselected tooth sought to be realigned from an initial position to a final position, said guiding cell having an upstream end surface and a downstream end surface, said guiding cell including:
        a guiding structure that comprises an alignment portion joined to the upstream and downstream end surfaces of the cell, the alignment portion comprising (a) a top wall for abutting a top of a cusp of the tooth and (b) side walls for guiding the tooth as the tooth is moved with respect to the side walls, from its initial position, closer to the upstream end surface, to its final position, closer to the downstream end surface, by the side walls laterally engaging the tooth; and
    a force providing element arranged within said guiding cell for urging the tooth to move from its initial position to its final position,
    wherein the guiding structure is configured to not deform during motion of the tooth from its initial position to its final position.

2. An appliance according to claim 1, wherein said base comprises a tray configured to be mounted over a plurality of teeth of the subject, and wherein when the tray is mounted onto the teeth of the subject, the guiding cell has a U-shaped cross-sectional configuration both in a buccal-lingual direction and in a mesiodistal direction.

3. An appliance according to claim 2, wherein:
an X-Y plane is defined as a plane in which buccal and lingual surfaces of the preselected tooth generally reside, an X-Z plane is defined as a mesiodistal plane of the preselected tooth, a Y-Z plane is defined as a plane that is perpendicular to the X-Y and X-Z planes,
  said upstream and downstream end surfaces of the guiding cell comprise first and second mutually opposing inward facing surfaces, each disposed generally in the X-Y plane,
said side walls define third and fourth, mutually opposing inward-facing lateral surfaces, formed integrally with and connecting between said first and second end surfaces, each of the pair of side walls disposed generally in the Y-Z plane,
said top wall is formed integrally with, and is connected to, said first, second, third and fourth surfaces, and is disposed generally in the X-Z plane, and
when said guiding cell is positioned over the tooth:
  the downstream end surface is operative to contact a predetermined first tooth surface of the lingual and buccal surfaces of the tooth when the tooth is at its final position, and
  the upstream end surface faces a second tooth surface of the lingual and buccal surfaces of the tooth and supports thereagainst said force providing element so as to apply an urging force to the second tooth surface in a lingual-buccal direction.

4. An appliance according to claim 3, and wherein
said force providing element is operative to apply a Z force vector along a Z axis, the Z-axis defined as being generally along the buccal-lingual axis, and
said appliance further comprises a resisting element configured to:
  be mounted onto a mounting-surface of the tooth such that the resisting element is facing said force providing element, and
  convert a portion of the Z force vector into a Y force vector by resisting the Z force vector, in order to retain the top of the cusp of the tooth in abutting engagement with said top wall.

5. An appliance according to claim 4, wherein said resisting element is a wedge-shaped baffle element configured to be affixed to the tooth mounting-surface such that the baffle element is facing said force providing element.

6. An appliance according to claim 3, wherein said force providing element includes:
  at least one extendable element joined at one end thereof to said upstream end surface and having a pressure face at a free end thereof for abutting the second tooth surface, said extendable element being extendable from a retracted position to an extended position whereat said free end is at least capable of abutting the second tooth surface; and
  an extending mechanism configured to extend said extendable element from the retracted position toward the extended position so as to apply an urging force to the tooth so as to move the tooth from its initial position to its final position.

7. An appliance according to claim 6, wherein said extendable element is an inflatable element.

8. An appliance according to claim 7, wherein said inflatable element has at least one elongated, balloon member adapted for positioning in a mesiodistal direction across one or more teeth sought to be realigned.

9. An appliance according to claim 8, wherein the balloon member is housed in said tray, and includes a discrete inflatable portion for applying an urging force to the preselected tooth.

10. An appliance according to claim 8, wherein the tray comprises a duct formed integrally with a sidewall of the tray, the duct defining at least one inward-facing opening in registration with the guiding cell, wherein the balloon member is an inner tube contained within the duct, and wherein the opening exposes a predetermined portion of said inner tube, thereby permitting inflation of said inner tube through said opening into said guiding cell, so as to apply an urging force to the preselected tooth.

11. An appliance according to claim 8, wherein said inflatable element comprises at least two elongated, balloon members, a first member being configured to be disposed along a buccal side of the tray and a second member being configured to be disposed along a lingual side of the tray.

12. An appliance according to claim 3, wherein said force providing element includes at least one spring, cantilevered from said upstream end and having an urging member at a free end thereof for abutting the second tooth surface of the lingual and buccal surfaces of the tooth.

13. An appliance according to claim 12, wherein said spring is a leaf spring.

14. An appliance according to claim 3, further comprising magnetic material for providing a magnetic field within the guiding cell.

15. An appliance according to claim 3, wherein said force providing element is adapted to provide a force at least:
  in a general direction from the initial position of the tooth to the final position of the tooth, and
  toward the top wall.

16. An appliance according to claim 15, wherein said force providing element is adapted to provide a force that is relatively constant during at least a part of operation of said appliance.

17. An appliance according to claim 15, wherein said force providing element is adapted to provide a force in a pulsating manner during at least a part of operation of said appliance.

18. An appliance according to claim 15, wherein said force providing element is adapted to provide a force that is substantially constant at least until the tooth reaches said downstream end surface.

19. An appliance according to claim 1, further comprising a static cell adapted for fitting over a tooth that is not to be moved and for maintaining the tooth that is not to be moved in its initial, position as the preselected tooth is realigned.

20. An appliance according to claim 1, and wherein said force providing element is further operative to apply to the preselected tooth a force vector predetermined so as to maintain the cusp of the tooth in abutting engagement with said top wall as the tooth is moved from its initial position to its final position.

* * * * *